(12) United States Patent
Burton et al.

(10) Patent No.: US 9,049,864 B2
(45) Date of Patent: Jun. 9, 2015

(54) PYRIDAZINONE HERBICIDAL COMPOUNDS

(71) Applicant: Syngenta Limited, Guildford, Surrey (GB)

(72) Inventors: Paul Burton, Bracknell (GB); Anthony Kozakiewicz, Bracknell (GB); James Morris, Bracknell (GB); Christopher John Mathews, Bracknell (GB); Stephen Shanahan, Bracknell (GB)

(73) Assignee: Syngenta Limited, Surrey (GB)

( * ) Notice: Subject to any disclaimer, the term of this patent is extended or adjusted under 35 U.S.C. 154(b) by 0 days.

(21) Appl. No.: 14/368,634

(22) PCT Filed: Apr. 12, 2013

(86) PCT No.: PCT/EP2013/057676
§ 371 (c)(1),
(2) Date: Jun. 25, 2014

(87) PCT Pub. No.: WO2013/160126
PCT Pub. Date: Oct. 31, 2013

(65) Prior Publication Data
US 2015/0031540 A1    Jan. 29, 2015

(30) Foreign Application Priority Data
Apr. 13, 2012 (GB) .................................. 1206598.3

(51) Int. Cl.
*C07D 403/04* (2006.01)
*A01N 43/58* (2006.01)
*A01N 43/54* (2006.01)

(52) U.S. Cl.
CPC .............. *A01N 43/54* (2013.01); *C07D 403/04* (2013.01); *A01N 43/58* (2013.01)

(58) Field of Classification Search
None
See application file for complete search history.

(56) References Cited

FOREIGN PATENT DOCUMENTS

WO   2009086041   7/2009
WO   2011045271   4/2011

OTHER PUBLICATIONS

International Search Report dated Jun. 28, 2013 for International Patent Application No. PCT/EP2013/057676.

*Primary Examiner* — Emily Bernhardt
(74) *Attorney, Agent, or Firm* — R. Kody Jones

(57) ABSTRACT

The present invention relates to compounds of Formula (I), or an agronomically acceptable salt of said compounds wherein $X^1$, $R^1$, $R^2$, $R^3$, $R^5$, G and n are as defined herein. The invention further relates to herbicidal compositions which comprise a compound of Formula (I), and to their use for controlling weeds, in particular in crops of useful plants.

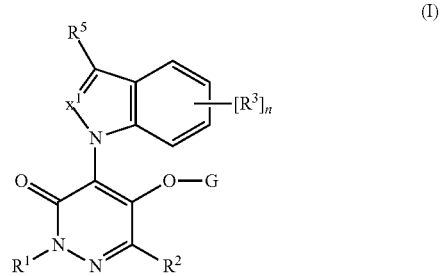

17 Claims, No Drawings

PYRIDAZINONE HERBICIDAL COMPOUNDS

RELATED APPLICATION INFORMATION

This application is a 371 of International Application No. PCT/EP2013/057676, filed 12 Apr. 2013, which claims priority to GB Application No. 1206598.3, filed 13 Apr. 2012, the contents of which are incorporated herein by reference herein.

The present invention relates to novel herbicidal compounds, to processes for their preparation, to herbicidal compositions which comprise the novel derivatives, and to their use for controlling weeds, in particular in crops of useful plants, or for inhibiting plant growth.

Herbicidal pyridazinones are known from WO2009/086041. In addition, herbicidal 5/6 membered heterocyclyl-substituted pyridazinones are known from WO 2011/045271. The present invention is based upon the identification of alternative heterocyclyl-substituted pyridazinones which exhibit improved herbicidal properties.

Thus, according to the present invention there is provided a compound of Formula (I):

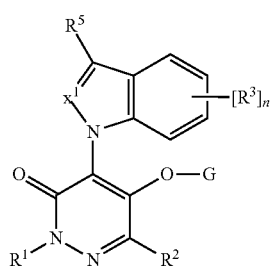

(I)

or an agronomically acceptable salt thereof,
wherein:—
$X^1$ is N or $CR^4$;
$R^1$ is selected from the group consisting of $C_1$-$C_4$ alkyl, $C_1$-$C_2$ alkoxy-$C_1$-$C_2$ alkyl, $C_2$-$C_4$ alkenyl, $C_1$-$C_4$ haloalkyl, $C_2$-$C_4$ haloalkenyl, $C_2$-$C_4$ alkynyl and $C_2$-$C_4$ haloalkynyl;
$R^2$ is selected from the group consisting of hydrogen, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$alkoxy-$C_1$-$C_3$alkoxy-$C_1$-$C_3$alkyl-, $C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, —S(O)$_p$C$_1$-C$_6$alkyl, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;
$R^3$ is independently selected from the group consisting of hydrogen, halogen, nitro, cyano, amino, $C_1$-$C_6$alkyl, $C_1$-$C_6$haloalkyl, $C_3$-$C_6$cycloalkyl, $C_1$-$C_6$alkoxy, $C_1$-$C_6$alkoxycarbonyl and —S(O)$_p$C$_1$-C$_6$ alkyl;
$R^4$ and $R^5$ are independently selected from the group consisting of hydrogen, hydroxyl, halogen, nitro, cyano, amino, $C_1$-$C_6$alkyl, $C_1$-$C_6$haloalkyl, $C_3$-$C_6$cyclo alkyl, $C_1$-$C_6$alkoxy, $C_1$-$C_6$alkoxycarbonyl and —S(O)$_p$C$_1$-$C_6$ alkyl;
G is hydrogen or —C(O)—$R^6$;
$R^6$ is selected from the group consisting of $C_1$-$C_6$alkyl, $C_1$-$C_6$alkenyl, $C_1$-$C_6$alkynyl, $C_1$-$C_6$alkyl-S—, $C_1$-$C_6$alkoxy, —NR$^7$R$^8$ and phenyl optionally substituted by one or more $R^9$;

$R^7$ and $R^8$ are independently selected from the group consisting of $C_1$-$C_6$ alkyl, $C_1$-$C_6$ alkoxy-;
wherein $R^7$ and $R^8$ can together form a morpholinyl ring;
$R^9$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy;
n=0, 1, 2, 3 or 4; and
p=0, 1 or 2.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

In a preferred embodiment of the present invention is a compound of Formula II (Formula I wherein G is hydrogen).

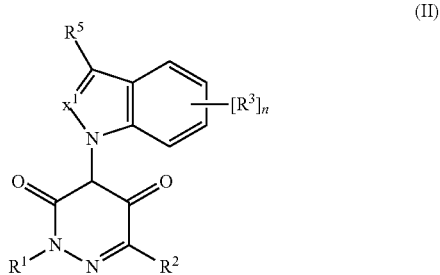

(II)

In another preferred embodiment of the present invention $R^2$ is selected from the group consisting of hydrogen, $C_1$-$C_6$alkyl, $C_1$-$C_6$haloalkyl, $C_1$-$C_6$alkoxy, $C_1$-$C_3$alkoxy-$C_1$-$C_3$alkyl, $C_3$-$C_6$cycloalkyl, $C_2$-$C_6$ alkenyl, $C_2$-$C_6$ haloalkenyl, $C_2$-$C_6$ alkynyl and $C_2$-$C_6$ haloalkynyl.

Particularly preferred is wherein $R^2$ is selected from the group consisting of hydrogen, methyl, ethyl, cyclopropyl and methoxymethyl, most preferably methyl.

In another embodiment of the present invention $R^2$ is hydrogen.

In another embodiment of the invention n=0.

In another embodiment of the invention $R^1$ is selected from the group consisting of methyl, ethyl and n-propyl.

In another embodiment of the present invention $X^1$ is N.

In another embodiment of the present invention $X^1$ is $CR^4$. Especially preferred is wherein $R^4$ is halogen (most preferably chlorine) and/or $R^5$ is halogen (most preferably chlorine).

Compounds of Formula I may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-

D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+triallate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methylaminocarbonyl)amino] benzenesulfonamide.

The safeners of the compound of Formula I may also be in the form of esters or salts, as mentioned e.g. in The Pesticide Manual, $14^{th}$ Edition (BCPC), 2006. The reference to cloquintocet-mexyl also applies to a lithium, sodium, potassium, calcium, magnesium, aluminium, iron, ammonium, quaternary ammonium, sulfonium or phos-phonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. In a particularly preferred aspect, the crop plant has been engineered to over-express homogentisate solanesyltransferase as taught in, for example, WO2010/029311.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. Weeds can also include plants which may be considered crop plants but which are growing outside a crop area ('escapes'), or which grow from seed left over from a previous planting of a different crop ('volunteers'). Such volunteers or escapes may be tolerant to certain other herbicides.

The compounds of the present invention can be prepared according to the following scheme(s).

Certain compounds of the present invention may be prepared from compounds of formula (1a), by heating with morpholine (Nagashima, Hiromu et al. Heterocycles, 26(1), 1-4; 1987) as shown in Reaction scheme 1.

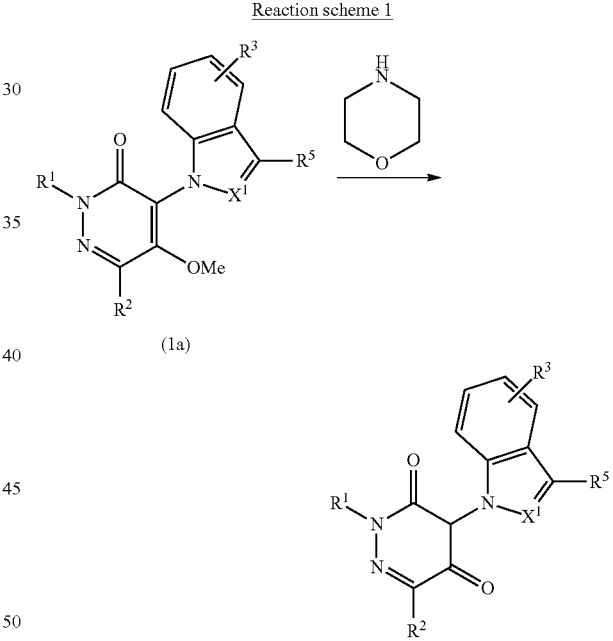

Compounds of formula (1a) may be prepared from compounds of formula (2) as shown in Reaction scheme 2.

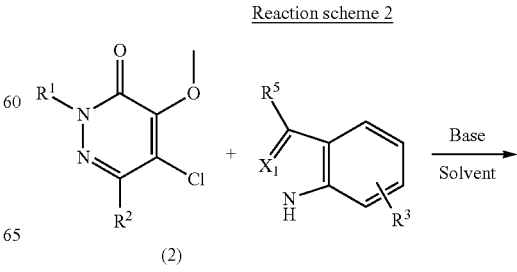

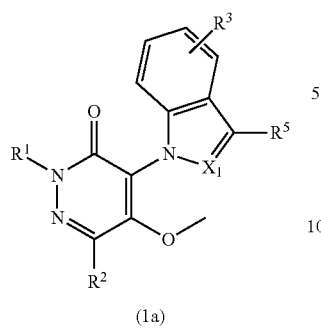

(1a)

Compounds of formula (1a) may be prepared by reacting pyridazinones (2) with the requisite fused-bicyclic heteroaromatic building block, in the presence of a strong base such as NaH or NaHMDS. Suitable solvents are THF or DMF.

The compound (2) where $R^1$=Me and $R^2$=H may be prepared by reaction of commercially available 4,5-Dichloro-2-methyl-3(2H)-pyridazinone with NaOMe in 1,4-dioxane, according to *Tetrahedron* 2001, 57, 1323-1330.

The compound (2) where $R^1$=Me and $R^2$=Me may be prepared as shown in reaction scheme 3.

Reaction scheme 3

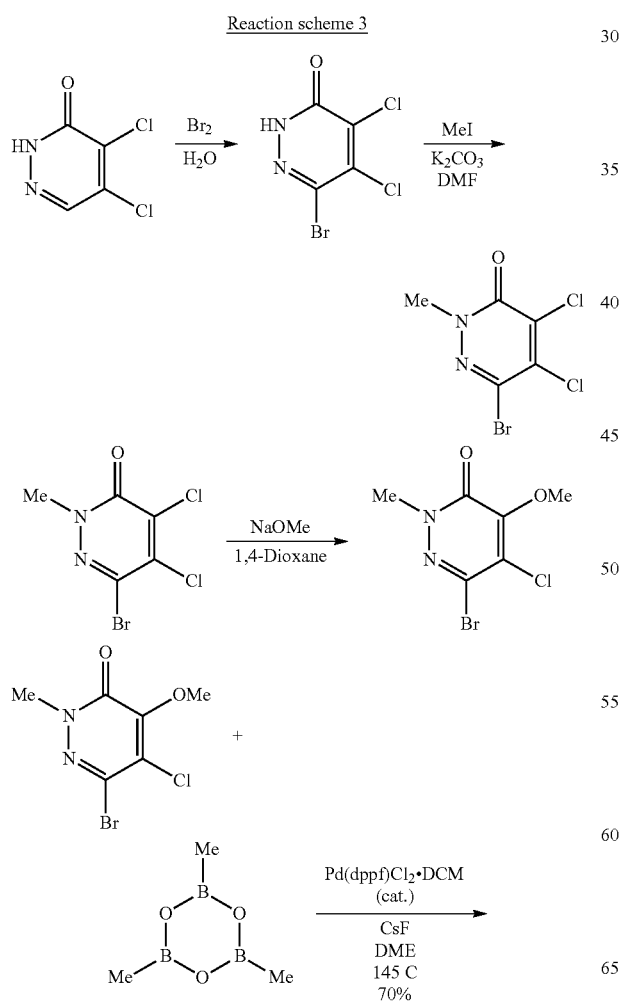

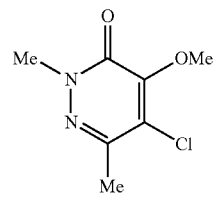

Alternatively, certain compounds of the present invention may be prepared according to Reaction scheme 4.

Reaction scheme 4

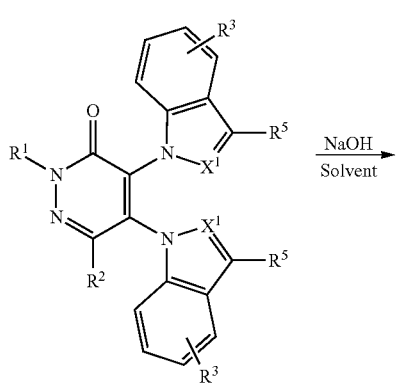

(3)

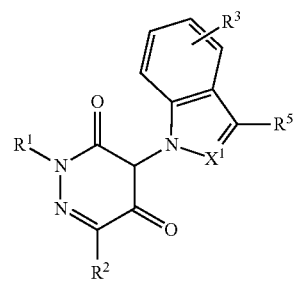

Compounds of the present invention may be prepared from compounds of formula (3) by heating with concentrated aqueous NaOH in a suitable solvent.

Compounds of formula (3) may be prepared as shown in Reaction scheme 5.

Reaction scheme 5

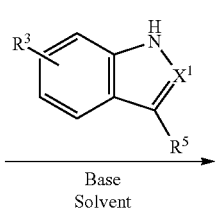

(4)

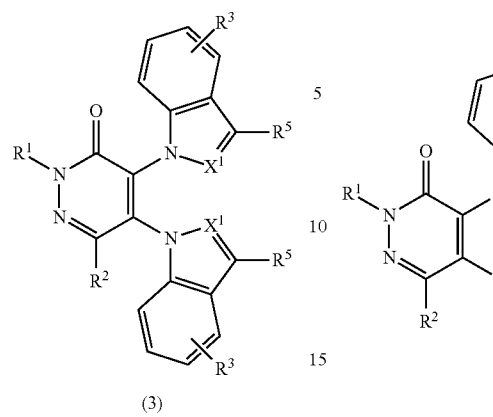

(3)

Compounds of formula (3) may be prepared by reacting compounds (4) with 2 or more equivalents of the requisite fused-bicyclic heteroaromatic building block, in the presence of a strong base and a suitable solvent. Examples of suitable bases are NaH, NaHMDS and Cs$_2$CO$_3$. Examples of suitable solvents are THF and DMF. An example of compounds (4) is commercially available 4,5-Dichloro-2-methyl-3(2H)-pyridazinone.

A variation used to access certain compounds of the present invention involves the mono- or bis-chlorination of Compounds (1b) as shown in Reaction scheme 6.

Reaction scheme 6

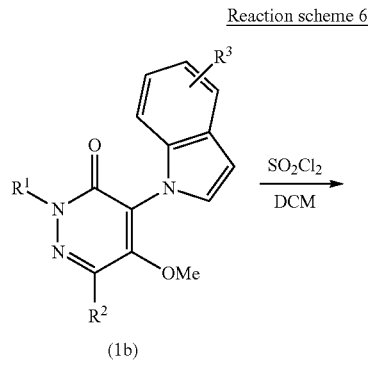

(1b)

Certain compounds of formula (1a) may be prepared by mono-bromination of mono-chloro compounds as shown in Reaction scheme 7.

Reaction scheme 7

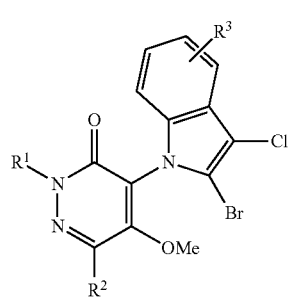

Certain compounds of formula (1a) may be prepared by tri-chlorination of compounds (1b) as shown in Reaction scheme 8.

Reaction scheme 8

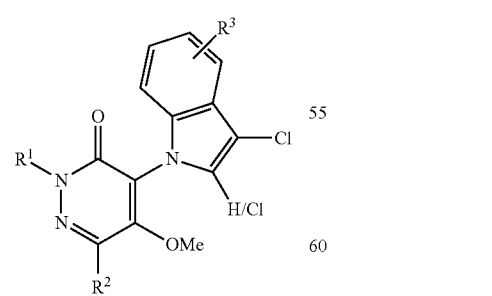

(1b)

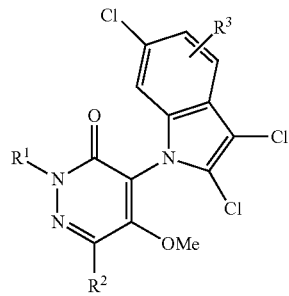

Certain compounds of formula (1a) may be prepared by the mono-bromination of compounds (1b) as shown in Reaction scheme 9.

Reaction scheme 9

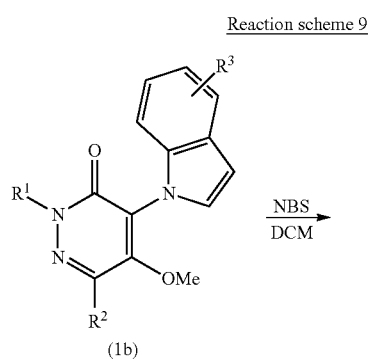

(1b)

Certain compounds of formula (1a) may be prepared by mono-chlorination of mono-bromo compounds as shown in Reaction scheme 10.

Reaction scheme 10

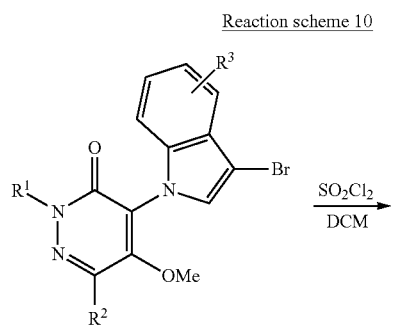

Certain compounds of formula (1a) may be prepared by bis- and tri-bromination of compounds (1b) as shown in Reaction scheme 11.

Reaction scheme 11

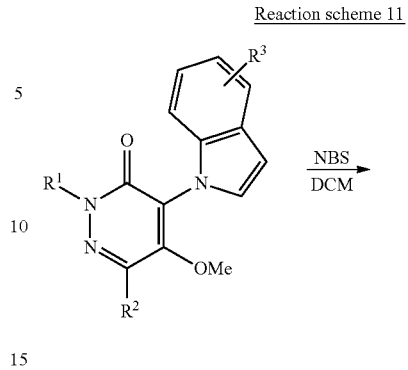

Certain compounds of formula (1a) may be prepared by reacting a bromide compound with a suitable coupling partner using a suitable catalyst/ligand, base and solvent as shown in Reaction scheme 12. Examples of suitable catalyst/ligands are Pd$_2$dba$_3$/XantPhos, [Pd(allyl)Cl]$_2$/RockPhos or tBuX-Phos precatalyst. Examples of suitable bases are DIPEA, LiHMDS, or Cs$_2$CO$_3$. Examples of suitable solvents are 1,4-dioxane, THF, DMF or toluene.

Reaction scheme 12

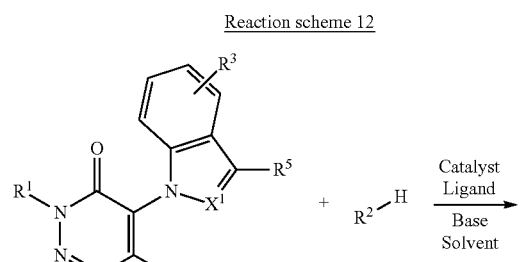

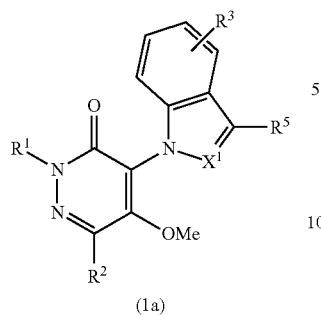

(1a)

Certain compounds of formula (1a) may be prepared by reacting a bromide compound with a suitable organoboron coupling partner using a suitable catalyst/ligand, base and solvent as shown in Reaction scheme 13. Examples of suitable organoboron coupling partners are boronic acids, boronic esters and potassium trifluoroborate salts. Examples of suitable catalyst/ligands are Pd(OAc)$_2$/RuPhos or Pd-dppf. An example of a suitable base is CsF. Examples of suitable solvents are 1,4-dioxane, water, or DME.

Reaction scheme 13

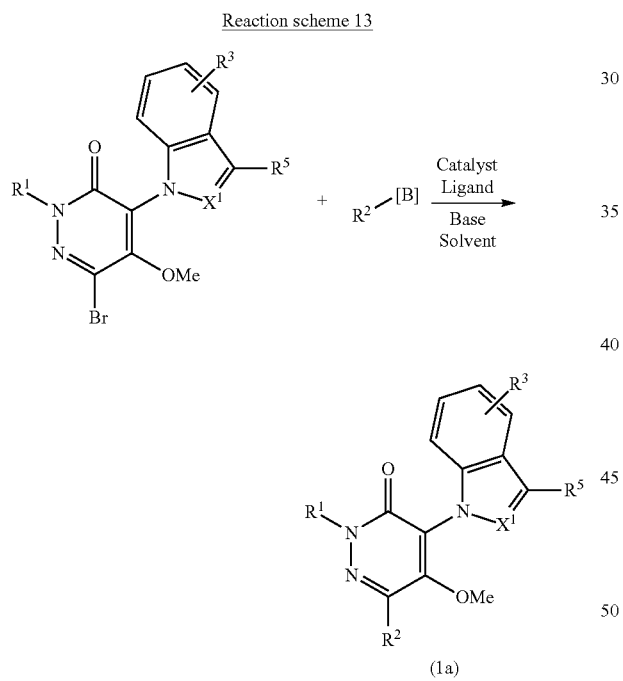

(1a)

Suitable potassium trifluoroborate salts are commercially available or may be prepared by reacting trifluoroethanol with potassium (bromomethyl)trifluoroborate, both commercially available, as shown in Reaction scheme 14.

Reaction scheme 14

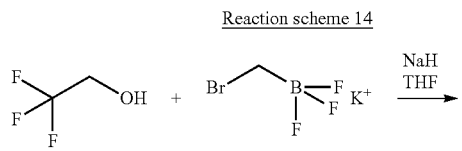

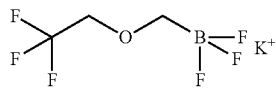

Certain methylsulfide compounds may be prepared by cross coupling of NaSMe with a bromide compound as shown in Reaction scheme 15.

Reaction scheme 15

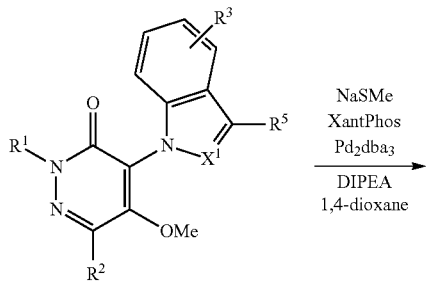

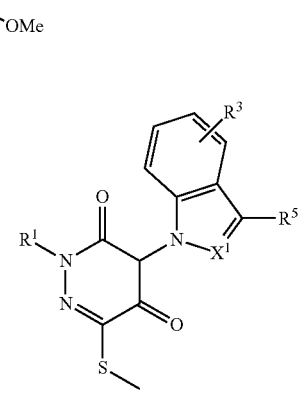

Certain compounds of formula (1a) may be prepared by sulphur oxidation as shown in Reaction scheme 16, (n=1 or 2).

Reaction scheme 16

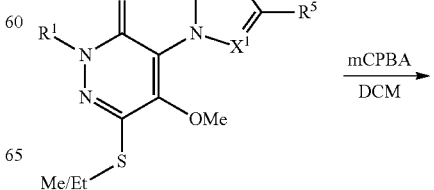

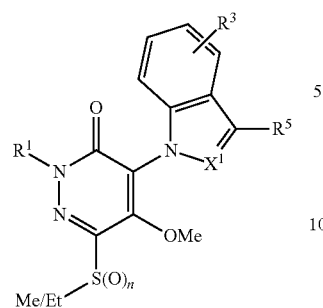

Certain compounds of formula (1a) may be prepared by reduction of an iso-propenyl compound as shown in Reaction scheme 17.

Reaction scheme 17

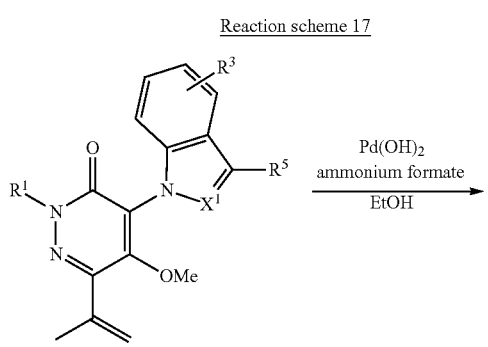

Certain compounds of formula (1a) may be prepared by nitrile formation as shown in Reaction scheme 18. (The required aldehyde starting material is prepared according to Reaction scheme 21)

Reaction scheme 18

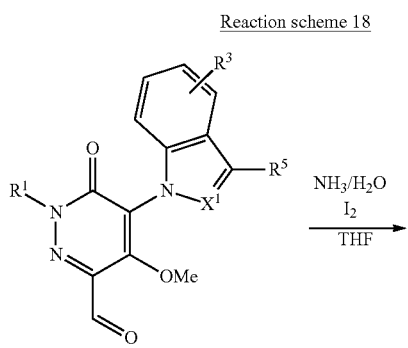

Certain compounds of the present invention may be prepared as shown in Reaction scheme 19.

Reaction scheme 19

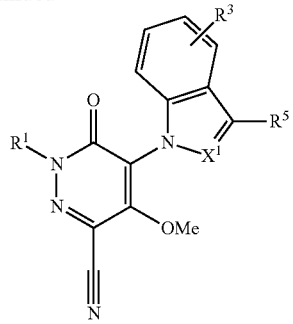

With reference to Reaction scheme 19, certain compounds of the present invention may be prepared by a final dione derivatisation step. The dione substrate is reacted with 1 or more equivalents of the requisite electrophilic species R—X, in the presence of NEt$_3$ and a suitable solvent at a temperature between 0° C. to reflux. Examples of suitable solvents are DCM and THF. Examples of suitable commercially available electrophilic species R—X are acyl chlorides, chloroformates, sulfonyl chlorides, amine carbonyl chlorides, alkyl halides and S-alkyl chlorothioformates.

Certain compounds of formula (1a) may be prepared by the mono-chlorination or mono-bromination of indole intermediates already substituted at the indole 2-position, as shown in Reaction scheme 20.

Reaction scheme 20

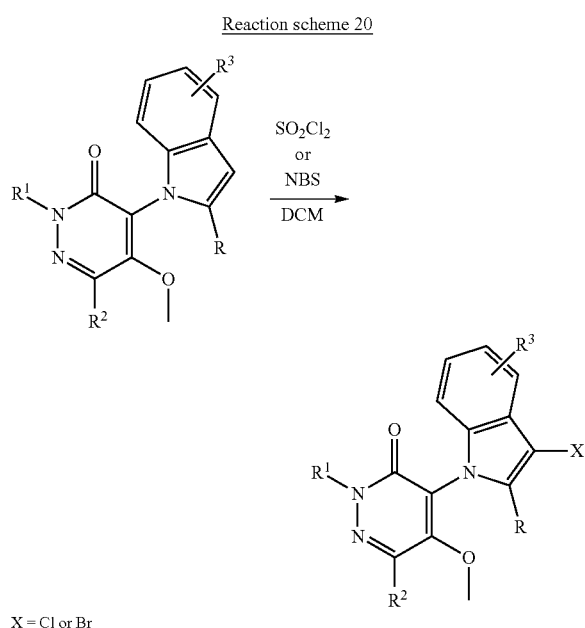

X = Cl or Br

Certain compounds of formula (1a) may be prepared by ozonolysis of alkenes, as shown in Reaction scheme 21.

Reaction scheme 21

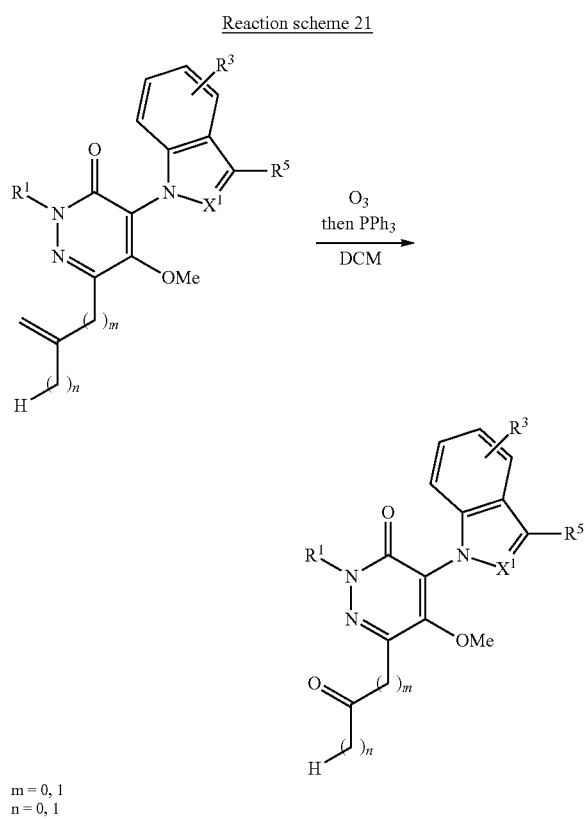

m = 0, 1
n = 0, 1

Certain compounds of formula (1a) may be prepared by the difluorination of carbonyl compounds, as shown in Reaction scheme 22. The carbonyl compound is reacted with 2 or more equivalents of diethylaminosulfur trifluoride (DAST), in a suitable solvent, at −78° C. to 25° C. Examples of suitable solvents are dichloromethane and chloroform. (The carbonyl compound starting material is typically prepared according to Reaction scheme 21).

Reaction scheme 22

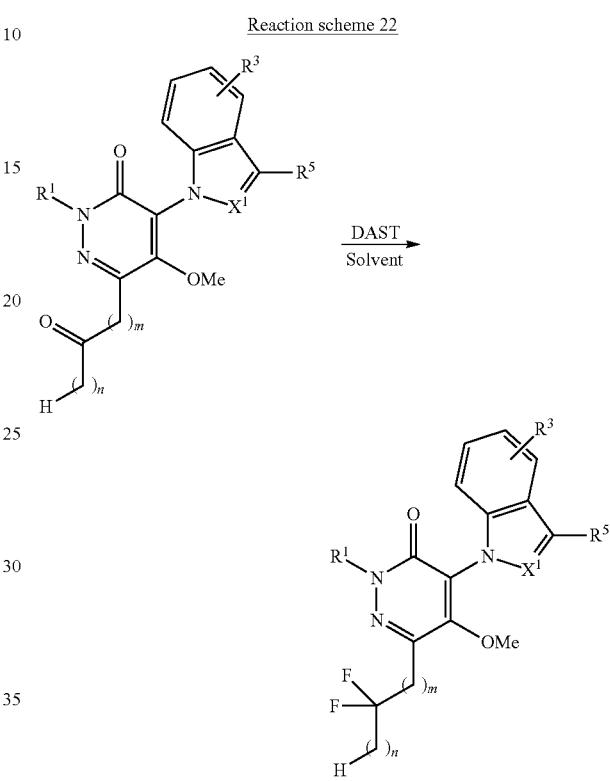

m = 0, 1
n = 0, 1

Certain compounds of formula (1a) may be prepared by the reduction of carbonyl compounds, as shown in Reaction scheme 23. The carbonyl compound substrate is reacted with 0.5 or more equivalents of sodium borohydride, in a suitable solvent, at −78° C. to 25° C. Examples of suitable solvents are methanol and ethanol.

Reaction scheme 23

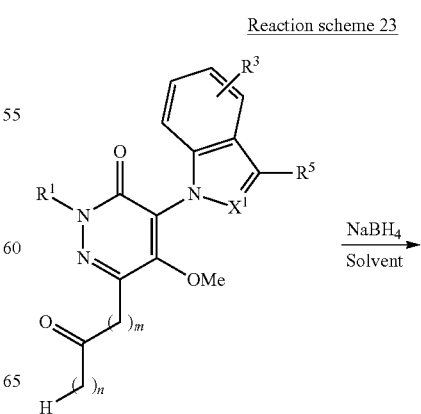

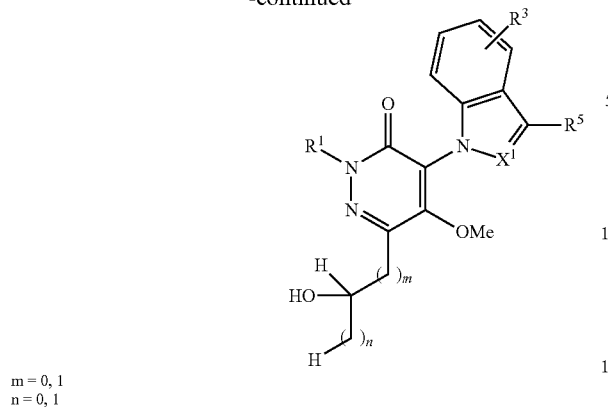

m = 0, 1
n = 0, 1

Certain compounds of formula (1a) may be prepared by the methylation of alcohols, as shown in Reaction scheme 24. The alcohol starting material is reacted with 1 or more equivalents of iodomethane, in the presence of a suitable base, in a suitable solvent, at −78° C. to 25° C. An example of a suitable base is sodium hydride. Examples of suitable solvents are N,N-dimethylformamide and tetrahydrofuran. (The alcohol substrate is typically prepared according to Reaction scheme 23)

Reaction scheme 24

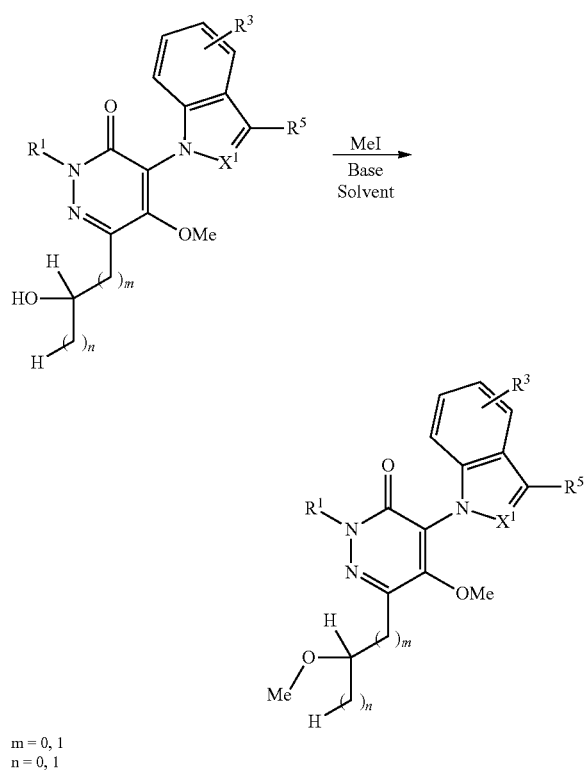

m = 0, 1
n = 0, 1

Certain compounds of formula (1a) may be prepared by the fluorination of alcohols, as shown in Reaction scheme 25. The alcohol starting material is reacted with 1 or more equivalents of diethylaminosulfur trifluoride (DAST), in a suitable solvent, at −78° C. to 25° C. Examples of suitable solvents are dichloromethane and chloroform.

Reaction scheme 25

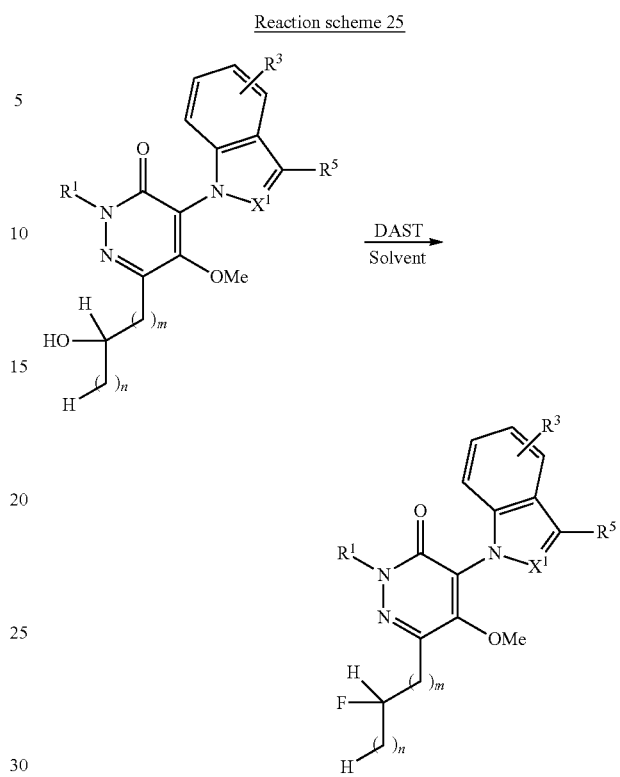

m = 0, 1
n = 0, 1

EXAMPLES

Example 1

4-(3-Chloro-indol-1-yl)-2-methyl-2H-pyridazine-3,5-dione

A mixture of 4-(3-Chloro-indol-1-yl)-5-methoxy-2-methyl-2H-pyridazin-3-one (1.70 g, 5.87 mmol) and morpholine (8 ml) is heated to 140° C. under microwave irradiation for 10 min. The mixture is allowed to cool then evaporated under reduced pressure to remove most of the morpholine. The residue is stirred with 1:1 v/v glacial AcOH:DCM (100 ml) to give a free-flowing semi-solid. Volatiles are removed in-vacuo and the solid obtained slurried with water. The solid is recovered by filtration under reduced pressure and dried at 1 mBar and 60° C. to give the title compound as a beige solid, 1.54 g, 95% yield. $^1$H nmr (DMSO-d6) δ (ppm) 7.89 (1H, s), 7.57-7.50 (2H, m), 7.24-7.17 (2H, m), 7.12-7.06 (1H, m), 3.66 (3H, s)

(Certain other compounds of the present invention also prepared according to Reaction scheme 1, may variously require modified purification procedures such as the use of column chromatography on silica, prep-HPLC or crystallisation).

4-(3-Chloro-indol-1-yl)-5-methoxy-2-methyl-2H-pyridazin-3-one

Sodium hydride (60% mass in mineral oil, 874 mg, 21.9 mmol) is suspended in dry DMF (10 ml) under $N_2$. With stirring, a solution of 3-chloroindole (3.01 g, 19.9 mmol) in DMF (30 ml) is added over 20 min. During the addition, cooling is employed by means of a water bath at ambient temperature. Gas evolution is observed and the mixture stirred for 30 min.

The reaction mixture is then diluted with further DMF (20 ml). A solution of 5-Chloro-4-methoxy-2-methyl-2H-pyridazin-3-one (3.47 g, 19.9 mmol) in DMF (30 ml) is added over 5 min. The mixture is then stirred for a further 3 h at ambient temperature before being cooled in an ice bath and quenched with saturated aqueous $KH_2PO_4$ (100 ml). The mixture is extracted into EtOAc (3×150 ml) and the combined organic extracts dried over $MgSO_4$. Evaporated in vacuo to afford a crude residue which is purified by flash chromatography (silica gel, eluant a 0-100% EtOAc in Isohexane gradient). The title compound was obtained as a beige coloured solid, 3.41 g, 59% yield. $^1$H nmr ($CDC_3$) δ (ppm) 7.92 (1H, s), 7.62-7.67 (1H, m), 7.20-7.28 (3H, m), 6.96-7.01 (1H, m), 3.86 (3H, s), 3.85 (3H, s).

Example 2

4-(3-chloroindazol-1-yl)-2-methyl-pyridazine-3,5-dione

A 1:1 w/w 32% NaOH:water mixture (8 g total) is added to 4,5-bis(3-chloroindazol-1-yl)-2-methyl-pyridazin-3-one (768 mg, 1.87 mmol) in methanol (30 mL) and then the mixture heated at 80° C. for 20 minutes. The mixture is allowed to cool to room temperature then concentrated in vacuo. Dichloromethane (50 mL) and water (50 mL) are added to the residue and the organic layer removed. The aqueous layer is acidified to pH 1 with conc. HCl. then extracted with dichloromethane (40 mL×2). The combined organic extracts are passed through a phase separator cartridge and concentrated in vacuo to give the title compound as a white solid (490 mg). $^1$H nmr (DMSO-d6) δ (ppm) 7.93 (1 H, s) 7.71-7.79 (1 H, m) 7.45-7.54 (1 H, m) 7.26-7.38 (2 H, m) 3.66 (3 H, s). Some other dione products prepared analogously were triturated with ethyl acetate or ether.

4,5-bis(3-chloroindazol-1-yl)-2-methyl-pyridazin-3-one

A mixture of 4,5-dichloro-2-methyl-pyridazin-3-one (551 mg, 3.08 mmol), 3-chloro-1H-indazole (1.17 g, 7.70 mmol), and caesium carbonate (1.48 g, 7.70 mmol) in DMF (15 ml) is heated to 110° C. for 1 h. The reaction mixture is cooled then concentrated in vacuo. The reaction mixture is diluted with ethyl acetate (50 ml) and washed with water (50 mL) and brine (50 mL×2). The organic extract is dried over magnesium sulphate, filtered and concentrated in vacuo. The crude product is purified by chromatography on silica eluting with 0-95% ethyl acetate in isohexane to give the product as a light orange oil (940 mg). $^1$H NMR ($CDC_3$) δ (ppm) 8.36 (1 H, s) 7.45-7.62 (2 H, m) 7.34 (1 H, ddd) 7.08-7.20 (3 H, m) 7.04 (1 H, ddd) 6.68 (1 H, d) 3.97 (3 H, s).

Example Procedure According to Reaction Scheme 6-Dichlorination 4-(2,3-dichloroindol-1-yl)-5-methoxy-2,6-dimethyl-pyridazin-3-one To a stirred solution of 4-indol-1-yl-5-methoxy-2,6-dimethyl-pyridazin-3-one (175 mg, 0.650 mmol) in dichloromethane (4 mL) at RT is added sulfuryl chloride (116 μL, 1.43 mmol). The reaction mixture changed to pale brown. After stirring for 1 h, the reaction is cooled to 0° C. and then saturated aqueous $NaHCO_3$ (5 mL) is added dropwise. The colour changed to a pale yellow and it is stirred for 10 min. The mixture was then poured into dichloromethane (20 mL) and water (20 mL) and the layers are separated. The aqueous layer is re-extracted with dichloromethane (20 mL×2) and the combined organics were dried ($MgSO_4$) and concentrated under reduced pressure onto silica. Flash chromatography (combiflash, 10% EtOAc/isohexane on a GOLD column) afforded the desired product 4-(2,3-dichloroindol-1-yl)-5-methoxy-2,6-dimethyl-pyridazin-3-one (150 mg, 0.444 mmol, 68%) as a pale yellow solid. $^1$H NMR ($CDC_3$) δ (ppm) 7.60 (1H, m), 7.27-7.24 (2H, m), 6.98 (1H, m), 3.74 (3H, s), 3.46 (3H, s), 2.35 (3H, s).

Preparation of 5-chloro-4-methoxy-2,6-dimethyl-pyridazin-3-one according to Reaction scheme 3

5-chloro-4-methoxy-2,6-dimethyl-pyridazin-3-one 4,5-dichloro-1H-pyridazin-6-one (1.95 g, 11.8 mmol) and bromine (0.73 ml, 14.2 mmol) are suspended in water (10 ml) and the mixture heated under microwave irradiation to 180° C. for 30 min. The resulting reaction mixture is filtered and the crude solid obtained washed thoroughly with water, then DCM, to yield 3-bromo-4,5-dichloro-1H-pyridazin-6-one, 2.06 g, as a white solid (71.5% yield).

$^1$H NMR (DMSO-d6) δ ppm=13.88 (1H, br. s)

To a stirred solution of 3-bromo-4,5-dichloro-1H-pyridazin-6-one (12.5 g, 51.3 mmol) in DMF (75.0 ml) is added $K_2CO_3$ (10.7 g, 76.9 mmol) and iodomethane (10.9 g, 76.9 mmol, 4.79 ml). The resulting mixture is stirred at ambient temperature for 18 h.

The reaction mixture is then poured onto ice-water (300 ml) and the mixture stirred for 2 h. The resulting precipitate is collected by filtration then dried to give 6-bromo-4,5-dichloro-2-methyl-pyridazin-3-one (10.7 g) as a beige solid (77% yield).

$^1$H NMR ($CDC_3$) δ ppm=3.83 (3H, s)

6-bromo-4,5-dichloro-2-methyl-pyridazin-3-one (1.5 g, 5.8 mmol) is dissolved in 1,4-dioxane (150 ml). Sodium methoxide (1.5 ml, 25 mass % methanolic solution, 6.4 mmol) is added dropwise and the reaction stirred for 2 h. The mixture is concentrated to a volume of 50 ml then diluted with 50 ml EtOAc. It is washed with 2×35 ml aqueous saturated brine. The organic layer is dried thoroughly over sodium sulfate, filtered and concentrated in vacuo. The crude residue so obtained was purified by flash chromatography (silica gel, eluant a 0-10% EtOAc in Isohexane gradient) to afford 6-bromo-5-chloro-4-methoxy-2-methyl-pyridazin-3-one (960 mg) as a white solid (65% yield).

$^1$H NMR ($CDC_3$) δ ppm=3.75 (3 H, s) 4.32 (3 H, s)

6-bromo-5-chloro-4-methoxy-2-methyl-pyridazin-3-one (500 mg, 1.68 mmol, 85 mass % purity), CsF (509 mg, 3.353 mmol), trimethylboroxine (242 mg, 1.93 mmol) and [1,1'-Bis (Diphenylphosphino)ferrocene]palladium(II) dichloride dichloromethane adduct (140 mg, 0.168 mmol) are dissolved in 1,2-Dimethoxyethane (5 ml) under $N_2$. The mixture is heated to 145° C. under microwave irradiation for 30 min.

The resulting mixture is filtered through celite, washing with EtOAc. The solution is washed with 2×25.0 ml aqueous saturated brine. The organic layer is separated, dried over $Na_2SO_4$, filtered and concentrated in vacuo. The crude residue is purified by flash chromatography (silica gel, eluant a 0-20% EtOAc in Isohexane gradient). The title compound 5-chloro-4-methoxy-2,6-dimethyl-pyridazin-3-one was obtained as a pale yellow solid (212 mg, 67% yield).

$^1$H NMR (CDC$_3$) δ ppm=2.37 (3 H, s) 3.72 (3 H, s) 4.26 (3 H, s).

Example Procedure According to Reaction Scheme 7-Bromination of Chloro-Compound 5-methoxy-2,6-dimethyl-4-(2-bromo-3-chloroindol-1-yl)pyridazin-3-one Part of a solution of bromine (200 mg, 1.25 mmol) in DCM (4 mL) is added dropwise, slowly, to a solution of 4-(3-chloroindol-1-yl)-5-methoxy-2,6-dimethyl-pyridazin-3-one (184 mg, 0.606 mmol) in DCM (2 mL) at 0° C. The bromine decolourised as it was added and addition was continued cautiously until an orange colour just persisted. NaHCO$_3$ (0.5 g saturated solution in water) is added cautiously, followed by sufficient sodium metabisulphite to decolorise the excess bromine. The resulting reaction mixture was extracted with DCM (3×60 mL) and the combined DCM layers were filtered through MgSO$_4$ and concentrated in vacuo. The resulting yellow gum was purified by flash chromatography (combiflash, 0 to 30% DCM/EtOAc) to yield the desired pro duct 5-methoxy-2,6-dimethyl-4-(2-bromo-3-chloroindol-1-yl)pyridazin-3-one (115 mg, 0.301 mmol, 50% Yield) as a white solid.

$^1$H NMR (CDC$_3$) δ ppm=7.64-7.58 (1H, m), 7.28-7.20 (2H, m), 7.02-6.96 (1H, m), 3.74 (3H, s), 3.44 (3H, s), 2.35 (3H, s).

Example Procedure According to Reaction Scheme 8-Trichlorination 5-methoxy-2,6-dimethyl-4-(2,3,6-trichloroindol-1-yl)pyridazin-3-one A solution of SO$_2$Cl$_2$ (185 mg, 1.365 mmol) in DCM (2 mL+0.5 mL wash) is added dropwise to a solution of 4-(indol-1-yl)-5-methoxy-2,6-dimethyl-pyridazin-3-one (145 mg, 85% purity, 0.455 mmol) in DCM (1.5 mL) at 0° C. The solution went yellow and then orange. After stirring for 30 min the solution went yellow and the reaction mixture is allowed to warm over 1 h to ambient temperature and stirred for a further 21 h. The reaction mixture is concentrated in vacuo and the resulting gum was purified by flash chromatography (combiflash, 0 to 10% DCM/EtOAc) to yield the desired product 5-methoxy-2,6-dimethyl-4-(2,3,6-trichloroindol-1-yl)pyridazin-3-one (128 mg, 0.344 mmol, 75% Yield) as a white solid.

$^1$H NMR (CDC$_3$) δ ppm=7.52 (1H, d), 7.22 (1H, dd), 6.99 (1H, d), 3.74 (3H, s), 3.49 (3H, s), 2.35 (3H, s).

Example Procedure According to Reaction Scheme 9-Mono-Bromination 5-methoxy-2,6-dimethyl-4-(3-bromoindol-1-yl)pyridazin-3-one A solution of NBS (110 mg, 0.619 mmol) in DCM (3 mL) is added dropwise to a solution of 4-(indol-1-yl)-5-methoxy-2,6-dimethyl-pyridazin-3-one (197 mg, 85% purity, 0.619 mmol) in DCM (2 mL) at 0° C. The resulting reaction mixture is allowed to warm to ambient temperature, stirred for 2 h and then concentrated in vacuo. Purification by flash chromatography (combiflash, 0 to 10% DCM/EtOAc) afforded the first desired product 4-(3-bromoindol-1-yl)-5,6-dimethoxy-2-methyl-pyridazin-3-one (195 mg, 0.560 mmol, 90% yield) as a white solid.

$^1$H NMR (CDC$_3$) δ ppm=7.63-7.59 (1H, m), 7.34 (1H, s), 7.32-7.23 (2H, m), 7.07-7.03 (1H, m), 3.76 (3H, s), 3.25 (3H, s), 2.34 (3H, s).

Example Procedure According to Reaction Scheme 10-Chlorination of Bromo-Compound 5-methoxy-2,6-dimethyl-4-(2-chloro-3-bromoindol-1-yl)pyridazin-3-one A solution of SO$_2$Cl$_2$ (47 μl, 0.583 mmol) in DCM (2 mL) is added dropwise to a solution of 4-(3-bromoindol-1-yl)-5-methoxy-2,6-dimethyl-pyridazin-3-one (203 mg, 0.583 mmol) in DCM (6 mL) at 0° C. The solution went pale yellow. After stirring for 5 min the cooling bath is removed and the resulting reaction mixture stirred at ambient temperature for 2 h. The reaction mixture is shaken well with a solution of NaHCO$_3$. The layers are separated and the aqueous layer extracted with DCM (3×20 mL). The combined DCM layers were filtered through MgSO$_4$ and concentrated in vacuo. The resulting solid was purified by flash chromatography (combiflash, 0 to 10% DCM/EtOAc) to yield the desired product 5-methoxy-2,6-dimethyl-4-(2-chloro-3-bromoindol-1-yl)pyridazin-3-one (194 mg, 0.507 mmol, 87% Yield).

$^1$H NMR (CDC$_3$) δ ppm=7.57-7.52 (1H, m), 7.30-7.22 (2H, m), 7.00-6.95 (1H, m), 3.74 (3H, s), 3.45 (3H, s), 2.35 (3H, s).

Example Procedure According to Reaction Scheme 11-Bis- and Tribromination 5-methoxy-2,6-dimethyl-4-(2,3-dibromoindol-1-yl)pyridazin-3-one and 5-methoxy-2,6-dimethyl-4-(2,3,6-tribromoindol-1-yl)pyridazin-3-one A solution of NBS (360 mg, 2.02 mmol) in DCM (8 mL) is added dropwise to a solution of 4-(indol-1-yl)-5-methoxy-2,6-dimethyl-pyridazin-3-one (201 mg, 85% purity, 0.631 mmol) in DCM (2 mL) at 0° C. The resulting reaction mixture is allowed to warm to ambient temperature, stirred for 2 h and then concentrated in vacuo. Purification by flash chromatography (combiflash, 0 to 10% DCM/EtOAc) afforded the first desired product 4-(2,3-dibromoindol-1-yl)-5,6-dimethoxy-2-methyl-pyridazin-3-one (40 mg, 0.094 mmol, 15% yield) as a yellow solid.

$^1$H NMR (CDC$_3$) δ ppm=7.58-7.53 (1H, m), 7.28-7.21 (2H, m), 7.01-6.95 (1H, m), 3.74 (3H, s), 3.43 (3H, s), 2.35 (3H, s).

Repeated purification of isolated impure product by flash chromatography (combiflash, 0 to 40% EtOAc/isohexane) yielded 4-(2,3,6-tribromoindol-1-yl)-5,6-dimethoxy-2-methyl-pyridazin-3-one (104 mg, 0.206 mmol, 33% yield) as a white solid.

$^1$H NMR (CDC$_3$) δ ppm=7.42 (1H, d), 7.35 (1H, dd), 7.14 (1H, d), 3.75 (3H, s), 3.47 (3H, s), 2.36 (3H, s).

Example Procedure According to Reaction Scheme 12-Cross Coupling with Bromide Compound 4-(2,3-dichloroindol-1-yl)-5,6-dimethoxy-2-methyl-pyridazin-3-one 6-bromo-4-(2,3-dichloroindol-1-yl)-5-methoxy-2-methyl-pyridazin-3-one (0.200 g, 0.496 mmol), Pd2Cl2(allyl)2 (2.7 mg, 0.00744 mmol), ditert-butyl-[6-methoxy-3-methyl-2-(2,4,6-triisopropylphenyl)phenyl]phosphane (11.6 mg, 0.0248 mmol) and dicesium carbonate (0.243 g, 0.744 mmol)

are suspended in toluene (3 mL) and methanol (60 μL). The resulting reaction mixture is heated under microwave irradiation to 110° C. for 20 min. The resulting reaction mixture is filtered, washing with EtOAc and concentrated under reduced pressure onto silica. Purification by flash chromatography (combiflash, 0 to 30% EtOAc/isohexane) afforded the desired product 4-(2,3-dichloroindol-1-yl)-5,6-dimethoxy-2-methyl-pyridazin-3-one (0.116 g, 0.3275 mmol, 66% yield) as a brown oil.

$^1$H NMR (CDC$_3$) δ ppm=7.62-7.58 (1H, m), 7.28-7.22 (2H, m), 7.02-6.97 (1H, m), 3.98 (3H, s), 3.68 (3H, s), 3.60 (3H, s).

Example Procedure According to Reaction Schemes 17 and 13-Reduction of Iso-Propenyl Group and Cross-Coupling of Bromide Compound & Organoboron 5-indol-1-yl-6-isopropyl-5-methoxy-2-methyl-pyridazin-3-one To a stirred solution of 4-(2,3-dichloroindol-1-yl)-6-isopropenyl-5-methoxy-2-methyl-pyridazin-3-one (355 mg, 0.975 mmol) in ethanol (5.0 mL) is added ammonium formate (1.24 g) and 20% palladium hydroxide on carbon, (50% water by weight, 273 mg, 0.194 mmol). The resulting reaction mixture is stirred at ambient temperature for 1 h and then heated to 60° C. for 30 min. The resulting reaction mixture is allowed to cool and then filtered through celite, washing with ethanol and concentrated in vacuo. The resulting crude yellow solid was 4-indol-1-yl-6-isopropyl-5-methoxy-2-methyl-pyridazin-3-one (253 mg, 0.851 mmol, 87%), which was used without further purification.

$^1$H NMR (CDC$_3$) δ ppm=7.66-7.63 (1H, m), 7.30 (1H, d), 7.24-7.15 (2H, m), 7.05-7.02 (1H, m), 6.73 (1H, dd), 3.78 (3H, s), 3.24 (1H, m), 3.14 (3H, s), 1.28 (6H, m).

4-(2,3-dichloroindol-1-yl)-6-isopropenyl-5-methoxy-2-methyl-pyridazin-3-one 6-bromo-4-(2,3-dichloroindol-1-yl)-5-methoxy-2-methyl-pyridazin-3-one (0.600 g, 1.49 mmol), 1,1'-bis(diphenylphosphino)ferrocene-palladium(II)dichloride dichloromethane complex (0.0608 g, 0.0744 mmol) and cesium fluoride (0.476 g, 2.98 mmol) are suspending in DME (3 mL) and 2-isopropenyl-4,4,5,5-tetramethyl-1,3,2-dioxaborolane (330 μL, 1.79 mmol) is added. The resulting reaction mixture is heated under microwave irradiation to 150° C. for 20 min. The resulting reaction mixture is diluted with EtOAc (50 mL) and then washed with brine (50 mL). The organic layer was dried (MgSO$_4$) and then concentrated under reduced pressure onto silica. Purification by flash chromatography (combiflash, 0 to 20% EtOAc/isohexane) afforded the desired product 4-(2,3-dichloroindol-1-yl)-6-isopropenyl-5-methoxy-2-methyl-pyridazin-3-one (503 mg, 1.38 mmol, 93%) as a pale brown oil.

$^1$H NMR (CDC$_3$) δ ppm=7.62-7.59 (1H, m), 7.28-7.25 (2H, m), 7.01-6.98 (1H, m), 5.62 (1H, m), 5.47 (1H, m), 3.81 (3H, s), 3.42 (3H, m), 2.15 (3H, m).

Example Procedure According to Reaction Scheme 14-Formation of Boron Tetrafluoride Potassium Salt Potassium trifluoro(2,2,2-trifluoroethoxymethyl)boranuide To a suspension of sodium hydride (0.5377 g, 60 mass %, 13.44 mmol) in anhydrous THF (45 mL) at 0° C. is added dropwise 2,2,2-trifluoroethanol (1.345 g, 13.44 mmol). The resulting reaction mixture is slowly warmed to ambient temperature over 1 hour and then re-cooled to 0° C. Further potassium bromomethyl(trifluoro)boranuide (1.000 g, 4.481 mmol) is added in one portion and the resulting reaction mixture is stirred at ambient temperature for a further 22 h. The reaction is quenched with potassium hydrogen fluoride (2 mL, 4.5 M, 9.1 mmol) and stirred for 30 min. The suspension was concentrated in vacuo and diethyl ether was added to the solid residue. The resulting suspension is filtered, washing with more diethyl ether and the washed solid was re-dissolved in acetonitrile and filtered. The filtrate was concentrated in vacuo and triturated with diethyl ether to yield potassium trifluoro(2,2,2-trifluoroethoxymethyl)boranuide (0.950 g, 4.32 mmol, 96.4% Yield).

$^1$H NMR (DMSO-$_{d6}$) δ ppm=3.72-3.65 (m, 2 H), 2.67-2.63 (m, 2 H).

$^{19}$F NMR (DMSO-$_{d6}$) δ ppm=−72.7, −141.5.

Example Procedure According to Reaction Schemes 16 and 15-Oxidation of Sulfur and Cross Coupling of Bromide Compound with Thiolate Salt 4-(2,3-dichloroindol-1-yl)-5-methoxy-2-methyl-6-methylsulfinyl-pyridazin-3-one To a stirred solution of 4-(2,3-dichloroindol-1-yl)-5-methoxy-2-methyl-6-methylsulfanyl-pyridazin-3-one (60 mg, 0.16 mmol) in DCM (2 mL) at −20° C. is added mCPBA (36 mg, 0.17 mmol). After stirring for 10 min at this temperature, a yellow precipitate had appeared. The reaction was poured into a mixture of DCM (20 mL), sodium bicarbonate saturated solution (10 mL) and sodium thiosulphate saturated solution (10 mL), then stirred for 10 min. The resulting mixture was then passed through a phase separator and the DCM layer was concentrated under reduced pressure to afford the desired product 4-(2,3-dichloroindol-1-yl)-5-methoxy-2-methyl-6-methylsulfinyl-pyridazin-3-one (59 mg, 0.12 mmol, 95%) as a yellow solid, which was used without further purification.

$^1$H NMR (CDC$_3$) δ ppm=7.59-7.66 (1 H, m) 7.27-7.35 (2 H, m) 6.98-7.05 (0.6 H, m) 6.91-6.97 (0.4 H, m) 3.90 (3 H, m) 3.55 (3 H, m) 3.01 (3 H, m)

4-(2,3-dichloroindol-1-yl)-5-methoxy-2-methyl-6-methylsulfanyl-pyridazin-3-one and 4-(2,3-dichloroindol-1-yl)-2-methyl-6-methylsulfanyl-pyridazine-3,5-dione 6-bromo-4-(2,3-dichloroindol-1-yl)-5-methoxy-2-methyl-pyridazin-3-one (600 mg, 1.49 mmol), XantPhos (36 mg, 0.060 mmol), Pd$_2$dba$_3$ (28 mg, 0.030 mmol) and NaSMe (115 mg, 1.64 mmol) are suspended in dioxane (8 mL) and DIPEA (0.773 mL, 4.47 mmol) is added. The resulting reaction mixture was heated to 60° C. and within 2 minutes it became black. After stirring at this temperature for 1 h, the reaction mixture is warmed to 80° C. and stirred overnight. The reaction was allowed to cool and poured into DCM (100 mL) and 10% NaOH solution (100 mL). The layers were separated and the DCM layer was dried (MgSO4) and concentrated under reduced pressure onto silica and then purified by flash chromatography (20% EtOAc/isohexane) to give desired product 4-(2,3-dichloroindol-1-yl)-5-methoxy-2-methyl-6-methylsulfanyl-pyridazin-3-one (125 mg, 0.338 mmol, 23%) as a yellow crystalline solid.

¹H NMR (CDC₃) δ ppm=7.62-7.58 (1H, m), 7.27-7.24 (2H, m), 7.01-6.97 (1H, m), 3.78 (3H, s), 3.49 (3H, s), 2.48 (3H, s).

The NaOH aqueous layer was acidified with conc. HCl to cause a yellow precipitate to crash out. This precipitate was then extracted with DCM (100 mL×3) and the DCM layers were dried (MgSO₄) and concentrated in vacuo. The resulting crude residue was purified by preparatory HPLC(reverse phase fraction lynx) to yield the demethylated 4-(2,3-dichloroindol-1-yl)-2-methyl-6-methylsulfanyl-pyridazine-3,5-dione (34 mg, 0.064 mmol, 6%) as a pale brown solid.

¹H NMR (CDC₃) δ ppm=7.61-7.57 (1H, m), 7.27-7.21 (2H, m), 6.95-6.91 (1H, m), 3.73 (3H, s), 2.53 (3H, s).

Example Procedure According to Reaction Schemes 18 & 21-Nitrile Formation and Ozonolysis 5-(2,3-dichloroindol-1-yl)-4-methoxy-1-methyl-6-oxo-pyridazine-3-carbonitrile To a stirred solution of 5-(2,3-dichloroindol-1-yl)-4-methoxy-1-methyl-6-oxo-pyridazine-3-carbaldehyde (98 mg, 0.278 mmol) in THF (1.5 mL) is added ammonium hydroxide (30% aq. solution, 1.5 mL), followed by iodine (92 mg, 0.362 mmol), which caused a dark brown colour to appear. The resulting reaction mixture was stirred for 1 h and then quenched with NaHCO3 solution (5 mL) and Na2S2O3 solution (5 mL). This caused the reaction to change from dark brown to a clear pale yellow mixture. After stirring for 10 min the reaction was extracted with DCM (20 mL×2), dried (MgSO4) and concentrated under reduced pressure to afford the desired pro duct 5-(2,3-dichloroindol-1-yl)-4-methoxy-1-methyl-6-oxo-pyridazine-3-carbonitrile (82 mg, 0.235 mmol, 85%) as a yellow foam that crushed into a yellow solid.

¹H NMR (CDC₃) δ ppm=7.65-7.61 (1H, m), 7.34-7.28 (2H, m), 7.00-6.95 (1H, m), 3.86 (3H, s), 3.61 (3H, s).

5-(2,3-dichloroindol-1-yl)-4-methoxy-1-methyl-6-oxo-pyridazine-3-carbaldehyde

A 3-necked flask is charged with 4-(2,3-dichloroindol-1-yl)-5-methoxy-2-methyl-6-vinyl-pyridazin-3-one (418 mg, 1.19 mmol) and dichlormethane (10 mL). The flask was fitted with a thermometer, an inlet tube and an outlet tube connected to two Dreschel bottles, the latter of which contained a 10% aq. KI solution. The inlet tube was connected to the ozone generator (turned off). The airflow was turned on to give a steady bubbling through the reaction flask and out through the KI solution. The flask was cooled to −78° C. and once at this temperature, the ozone generator was turned on and bubbled for 10 min. The KI solution became darker over the course of the reaction. The ozone generator was turned off and the reaction purged with air for 2 min. It was then disconnected from the inlet and outlet tubes and triphenylphosphine (939 mg, 3.58 mmol) was added. The reaction was allowed to stir and gradually warm to RT over 1 h, then stirred at RT for a further 3 h and left to stand overnight. The resulting reaction mixture was concentrated onto silica and the purified by chromatography (combiflash, 0 to 50% EtOAc/ihexane) to give the desired product 5-(2,3-dichloroindol-1-yl)-4-methoxy-1-methyl-6-oxo-pyridazine-3-carb aldehyde (262 mg, 0.744 mmol, 63%) as a yellow solid.

¹H NMR (CDC₃) δ ppm=9.92 (1H, s), 7.64-7.60 (1H, m), 7.31-7.26 (2H, m), 7.00-6.96 (1H, m), 3.93 (3H, s), 3.57 (3H, s).

Example Procedure According to Reaction Scheme 19-Dione Derivatisation

[5-(2,3-dichloroindol-1-yl)-1,3-dimethyl-6-oxo-pyridazin-4-yl]isopropylsulfanylformate To a stirred suspension of 4-(2,3-dichloroindol-1-yl)-2,6-dimethyl-pyridazine-3,5-dione (120 mg, 0.370 mmol) in dichloromethane (8 mL) at RT is added triethylamine (129 μL, 0.925 mmol). The reaction mixture turned homogeneous. S-Isopropyl chlorothioformate (69 μL, 0.555 mmol) is added and the reaction mixture is stirred for 15 min. The mixture is then quenched with water (10 mL) and the layers are separated. The aqueous layer is re-extracted with dichloromethane (10 mL×3) and the combined organics were dried (phase separator cartridge) and concentrated under reduced pressure onto silica. Flash chromatography (combiflash, 0-20% EtOAc/isohexane) afforded the desired product [5-(2, 3-dichloroindol-1-yl)-1,3-dimethyl-6-oxo-pyridazin-4-yl] isopropylsulfanylformate (140 mg, 0.328 mmol, 89%) as yellow solid.

¹H NMR (CDC₃) δ (ppm) 7.52-7.57 (1H, m), 7.21-7.27 (2H, m), 6.94-6.98 (1H, m), 3.86 (3H, s), 3.22 (1H, sept), 2.38 (3H, s), 1.11 (3H, d), 1.04 (3H, d).

Example Procedure According to Reaction Scheme 20-Halogenation of 2-Substituted Indole 4-(3-chloro-2-methyl-indol-1-yl)-5-methoxy-2,6-dimethyl-pyridazin-3-one To a stirred solution of 5-methoxy-2,6-dimethyl-4-(2-methylindol-1-yl)pyridazin-3-one (147 mg, 0.52 mmol) in DCM (3 ml) at 0° C., was added dropwise a solution of sulfuryl chloride (70 mg, 0.52 mmol) in DCM (1 ml). Further DCM (1 ml) was added. After a reaction time of 1 h, the mixture was quenched by addition of sat. aqueous NaHCO₃ (2 ml). The resulting mixture was filtered through solid MgSO₄, washing with DCM. The filtration liquors were concentrated in vacuo to afford the title compound as a pale brown solid (158 mg, 96%). The material was used for subsequent reactions without further purification.

¹H NMR (CDC₃) δ (ppm) 7.60-7.54 (1H, m), 7.22-7.16 (2H, m), 6.96-6.90 (1H, m), 3.75 (3H, s), 3.27 (3H, s), 2.34 (3H, s), 2.32 (3H, s).

Example Procedure According to Reaction Scheme 22-Difluorination of Carbonyl Compound 4-(2,3-dichloroindol-1-yl)-6-(difluoromethyl)-5-methoxy-2-methyl-pyridazin-3-one To a stirred solution of 5-(2,3-dichloroindol-1-yl)-4-methoxy-1-methyl-6-oxo-pyridazine-3-carbaldehyde (100 mg, 0.284 mmol) in DCM (3 mL) at 0° C. is added (diethylamino)sulfurtrifluoride (94 μL, 0.710 mmol). The reaction is allowed to warm to RT over 1 h. The reaction is quenched cautiously at 0° C. with water (5 mL) and then the dropwise addition of NaHCO₃ solution (5 mL). After stirring for 10 min it is extracted with DCM (20 mL), dried (MgSO₄) and concentrated under reduced pressure to give 4-(2,3-dichloroindol-1-yl)-6-(difluoromethyl)-5-methoxy-2-methyl-pyridazin-3-one (102 mg, 0.273 mmol, 96%) as a brown solid.

1H NMR (400 MHz, CDC₃): 7.64-7.59 (1H, m), 7.32-7.27 (2H, m), 7.01-6.97 (1H, m), 6.61 (1H, t), 3.82 (3H, s), 3.52 (3H, s).

Example Procedure According to Reaction Scheme 23-Reduction of Carbonyl Compound 4-(2,3-dichloroindol-1-yl)-6-(1-hydroxyethyl)-5-methoxy-2-methyl-pyridazin-3-one To a stirred solution of 6-acetyl-4-(2,3-dichloroindol-1-yl)-5-methoxy-2-methyl-pyridazin-3-one (500 mg, 1.37 mmol) in ethanol (1 mL) at 0° C. is added sodium borohydride (79 mg, 2.05 mmol). After stirring for 20 min, the reaction is quenched with water (10 mL), then concentrated under reduced pressure to remove most of the ethanol. The aqueous solution is then extracted with Et$_2$O (20 mL×2), then concentrated under reduced pressure to give the desired product 4-(2,3-dichloroindol-1-yl)-6-(1-hydroxyethyl)-5-methoxy-2-methyl-pyridazin-3-one (379 mg, 1.03 mmol, 75%) as a white solid.

1H NMR (400 MHz, CDCl3), 7.63-7.59 (1H, m), 7.31-7.22 (2H, m), 7.00-6.93 (1H, m), 5.05-4.97 (1H, m), 3.79 (3H, s), 3.47 (3H, s), 3.03-3.00 (1H, m), 1.56-1.53 (3H, m).

Example Procedure According to Reaction Scheme 24-Methylation of Alcohol Compound 4-(2,3-dichloroindol-1-yl)-5-methoxy-6-(1-methoxyethyl)-2-methyl-pyridazin-3-one To a stirred solution of 4-(2,3-dichloroindol-1-yl)-6-(1-hydroxyethyl)-5-methoxy-2-methyl-pyridazin-3-one (98 mg, 0.27 mmol) in DMF (1 mL) at 0° C. is added sodium hydride (60% dispersion in mineral oil, 32 mg, 0.80 mmol). After stirring for 5 min, MeI (50 µL, 0.80 mmol) is added. After 30 min, the reaction is cautiously quenched with ammonium chloride solution (10 mL) and allowed to stand overnight. The following day, the reaction mixture is extracted with DCM (10 mL×3), then dried (MgSO$_4$) and concentrated under reduced pressure. The residue is resubmitted to the reaction conditions with the same procedure and reagent/solvent quantities as above. After stirring for 30 min, it is warmed to RT and allowed to stir for a further 1.5 h. It is then cooled to 0° C. and then quenched cautiously with ammonium chloride solution (20 mL). Et$_2$O is then added and the layers were separated. The organic layer is washed with water (20 mL×3), then dried (MgSO$_4$) and concentrated under reduced pressure onto silica. Chromatography (0 to 30% EtOAc/isohexane) affords the desired product 4-(2,3-dichloroindol-1-yl)-5-methoxy-6-(1-methoxyethyl)-2-methyl-pyridazin-3-one (64 mg, 0.168 mmol, 63%) as a colourless oil.

1H NMR (400 MHz, CDC$_3$): 7.63-7.58 (1H, m), 7.30-7.24 (2H, m), 7.01-6.94 (1H, m), 4.66-4.62 (1H, m), 3.80 (3H, s), 3.45-3.43 (6H, m), 1.56-1.54 (3H, m).

Example Procedure According to Reaction Scheme 25-Fluorination of Alcohol Compound.

4-(2,3-dichloroindol-1-yl)-6-(1-fluoroethyl)-5-methoxy-2-methyl-pyridazin-3-one

To a stirred solution of 4-(2,3-dichloroindol-1-yl)-6-(1-hydroxyethyl)-5-methoxy-2-methyl-pyridazin-3-one (185 mg, 0.502 mmol) in DCM (4 mL) at 0° C. is added (diethylamino)sulfurtrifluoride (86 µL, 0.65 mmol). After stirring for 30 min, the reaction is quenched cautiously at 0° C. with the dropwise addition of NaHCO$_3$ solution (10 mL). After stirring for 10 min it is extracted with DCM (20 mL), dried (MgSO$_4$) and concentrated under reduced pressure. Chromatography (0 to 20% EtOAc/isohexane) gives the desired product 4-(2,3-dichloroindol-1-yl)-6-(1-fluoroethyl)-5-methoxy-2-methyl-pyridazin-3-one (194 mg, 0.524 mmol, 104%). 1H NMR analysis showed a ~10% impurity, which was separated after the subsequent step.

1H NMR (400 MHz, CDC$_3$): 7.63-7.59 (1H, m), 7.30-7.24 (2H, m), 7.01-6.94 (1H, m), 5.91-5.73 (1H, m), 3.81 (3H, s), 3.48 (3H, s), 1.75 (3H, dd).

TABLE 1

Examples of herbicidal compounds of the present invention.

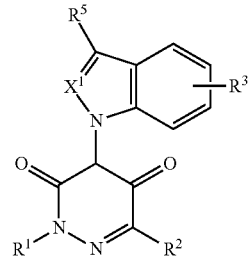

| Compound | $X^1$ | $R^4$ | $R^5$ | $R^1$ | $R^2$ | $R^3$ | NMR |
|---|---|---|---|---|---|---|---|
| 1.001 | N | — | —Cl | —CH$_3$ | H | — | (DMSO-d6) 7.93 (1H, s) 7.71-7.79 (1H, m) 7.45-7.54 (1 H, m) 7.26-7.38 (2H, m) 3.66 (3H, s) |
| 1.002 | CR$^4$ | H | H | —CH$_3$ | —CH$_3$ | — | (CDCl$_3$) 7.69 (1H, d), 7.30-7.19 (3H, m), 7.02 (1H, d), 6.76 (1H, d), 3.75 (3H, s), 2.39 (3H, s) |
| 1.003 | CR$^4$ | —Cl | —Cl | —CH$_3$ | —CH$_3$ | — | (CDCl$_3$) 7.57-7.52 (1H, m), 7.24-7.15 (2H, m), 6.81-6.77 (1H, m), 3.47 (3H, s), 2.21 (3H, s) |
| 1.004 | CR$^4$ | H | H | —CH$_3$ | H | 5-Br | (d4MeOH) 7.86 (1H, s), 7.73 (1H, d), 7.26 (1H, d), 7.23 (1H, dd), 6.97 (1H, d), 6.62 (1H, dd), 3.76 (3H, s) |
| 1.005 | CR$^4$ | H | H | —CH$_3$ | H | 4-Br | (d4MeOH) 7.60 (1H, s), 7.24 (1H, d), 7.19 (1H, dd), 7.02-6.95 (2H, m), 6.59 (1H, dd), 3.68 (3H, s) |

TABLE 1-continued

Examples of herbicidal compounds of the present invention.

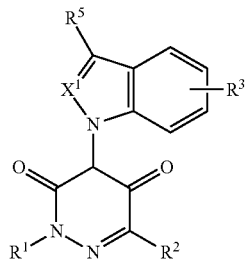

| Compound | X¹ | R⁴ | R⁵ | R¹ | R² | R³ | NMR |
|---|---|---|---|---|---|---|---|
| 1.006 | CR⁴ | H | H | —CH₃ | H | 6-Br | (d4MeOH) 7.79 (1H, s), 7.48 (1H, dd), 7.20 (1H, d), 7.18-7.15 (2H, m), 6.62 (1H, d), 3.75 (3H, s) |
| 1.007 | CR⁴ | H | —CH₃ | —CH₃ | H | — | (d4MeOH) 7.87 (1H, s), 7.53 (1H, dd), 7.15-7.07 (2H, m), 6.99-6.96 (2H, m), 3.76 (3H, s), 2.34 (3H, s) |
| 1.008 | CR⁴ | H | H | —CH₃ | H | 7-Me | (d4MeOH) 7.80 (1H, s), 7.36 (1H, d), 6.91-6.88 (2H, m), 6.80 (1H, d), 6.56 (1H, d), 3.69 (3H, s), 2.17 (3H, s) |
| 1.009 | N | — | H | —CH₃ | H | — | (d4MeOH) 8.26 (1H, d), 7.91 (1H s), 7.83 (1H, dt), 7.43 (1H, td), 7.27-7.22 (2H, m), 3.78 (3H, s) |
| 1.010 | CR⁴ | H | —Cl | -Pr | H | — | (CDCl₃) 7.74 (1H, s), 7.61 (1H, d), 7.20-7.12 (2H, m), 6.97 (1H, d), 6.65 (1H, d), 5.18-5.14 (1H, m), 1.35 (6H, d) |
| 1.011 | CR⁴ | H | —Cl | —CH₂OCH₃ | H | — | (d4MeOH) 8.26 (1H, s), 7.58 (1H, dd), 7.24 (1H, d), 7.14-7.02 (2H, m), 6.63 (1H, dd), 3.92 (2H, s), 2.65 (3H, s) |
| 1.012 | CR⁴ | H | —Cl | —CH₃ | H | — | (DMSO-d6) 7.89 (1H, s), 7.57-7.50 (2H, m), 7.24-7.17 (2H, m), 7.12-7.06 (1H, m), 3.66 (3H, s) |
| 1.013 | CR⁴ | —Cl | —Cl | —CH₃ | H | — | (CDCl₃) 7.48 (1H, s), 7.48-7.43 (1H, m), 7.18-7.11 (2H, m), 6.76-6.70 (1H, m), 3.60 (3H, s) |
| 1.014 | CR⁴ | H | H | —CH₃ | H | — | (DMSO-d6) 7.94 (1H, s), 7.59 (1H, dd), 7.31 (1H, d), 7.13-7.06 (2H, m), 7.05 (1H, dd), 6.62 (1H, d), 3.68 (3H, s) |
| 1.015 | N | — | H | —CH₃ | H | 4-Cl | (CDCl₃) 10.51 (1 h, s), 8.40 (1 H, d), 7.83 (1 H, s), 7.67 (1 H, d), 7.43 (1 H, dd), 7.28 (1 H, dd), 3.88 (3 H, s) |
| 1.016 | CR⁴ | H | Cl | —CH₃ | H | 5-Cl | (DMSO-d6) 7.91 (1H, s), 7.64 (1H, s), 7.55-7.56 (1H, d), 7.24-7.26 (1H, dd), 7.14-7.16 (1H, d), 3.67 (3H, s) |
| 1.017 | CR⁴ | H | H | —CH₃ | H | 5-Cl | (DMSO-d6) 7.90 (1H, s), 7.64 (1H, s), 7.39-7.40 (1H, d), 7.03-7.13 (2H, m), 6.60-6.61 (1H, d), 3.67 (3H, s) |
| 1.018 | CR⁴ | H | —Cl | -tert-butyl | H | — | (CDCl₃) 7.49 (1H, s), 7.39 (1H, d), 7.29-7.20 (3H, m), 6.95 (1H, d), 1.51 (9H, s). |
| 1.019 | CR⁴ | H | —Cl | —CH₃ | iPr | — | (CDCl₃) 7.71 (1H, m), 7.33-7.27 (2H, m), 7.23 (1H, s), 7.01-6.98 (1H, m), 3.75 (3H, s), 3.24 (1H, septet), 1.33-1.28 (6H, m). |
| 1.020 | CR⁴ | Cl | Cl | —CH₃ | —CH₃ | 6-Cl | (CDCl₃) 8.11 (1H, br s), 7.44 (1H, d), 7.18 (1H, dd), 6.79 (1H, d), 3.43 (3H, s), 2.18 (3H, s) |
| 1.021 | CR⁴ | Cl | Br | —CH₃ | —CH₃ | — | (CDCl₃) 7.54-7.48 (1H, m), 7.27-7.17 (2H, m), 6.87-6.80 (1H, m), 3.55 (3H, s), 2.27 (3H, s) |

TABLE 1-continued

Examples of herbicidal compounds of the present invention.

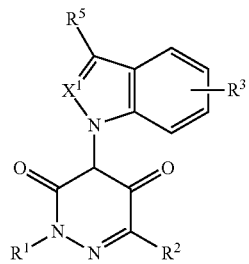

| Compound | X¹ | R⁴ | R⁵ | R¹ | R² | R³ | NMR |
|---|---|---|---|---|---|---|---|
| 1.022 | CR⁴ | Br | Br | —CH₃ | —CH₃ | 5-Br | (MeCN-d3) 7.72 (1H, d), 7.37 (1H, dd), 7.01 (1H, d), 3.63 (3H, s), 2.31 (3H, s) |
| 1.023 | CR⁴ | Br | Br | —CH₃ | —CH₃ | 6-Br | (DMSO-d6) 12.0 (1H, br s), 7.41 (1H, d), 7.39 (1H, s), 7.35 (1H, dd), 3.58 (3H, s), 2.26 (3H, s) |
| 1.024 | CR⁴ | Br | Br | —CH₃ | —CH₃ | — | (CDCl₃) 7.46 (1H, dd), 7.14 (2H, m), 6.78 (1H, dd), 4.95 (1H, br s), 3.43 (3H, s), 2.13 (3H, s) |
| 1.025 | CR⁴ | H | Br | —CH₃ | —CH₃ | — | (DMSO-d6) 11.4 (1H, bs), 7.47 (1H, s), 7.45-7.39 (1H, m), 7.19-7.11(2H, m), 7.04-6.98 (1H, m), 3.54 (3H, s), 2.22 (3H, s) |
| 1.026 | CR⁴ | Br | Cl | —CH₃ | —CH₃ | — | (CDCl₃) 7.58-7.54 (1H, m), 7.22-7.14 (2H, m), 6.83-6.78 (1H, m), 3.49 (3H, s), 2.22 (3H, s) |
| 1.027 | CR⁴ | H | Cl | —CH₃ | —CH₃ | — | (DMSO-d6) 11.4 (1H, bs), 7.54-7.47 (1H, m), 7.45 (1H, s), 7.20-7.10 (2H, m), 7.05-6.97 (1H, m), 3.54 (3H, s), 2.22 (3H, s) |

TABLE 2

Examples of herbicidal compounds of the present invention.

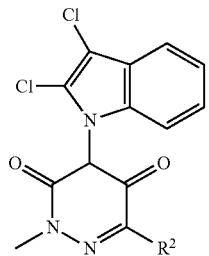

| Compound | R² | NMR |
|---|---|---|
| 2.001 | —C≡N | (d4MeOH) 7.58-7.55 (1H, m), 7.28-7.22 (2H, m), 7.13-7.09 (1H, m), 3.80 (3H, s) |
| 2.002 | —CHF₂ | (CDCl₃) 7.62-7.58 (1H, m), 7.29-7.24 (2H, m), 6.93-6.90 (1H, m), 6.57 (1H, t), 3.74 (3H, s). |
| 2.003 | —S—CH₃ | (CDCl₃) 7.61-7.57 (1H, m), 7.27-7.21 (2H, m), 6.95-6.91 (1H, m), 3.73 (3H, s), 2.53 (3H, s) |
| 2.004 | —S(O)₂CH₃ | (CDCl₃) 7.62-7.59 (1H, m), 7.28-7.23 (2H, m), 6.97-6.93 (1H, m), 3.95 (3H, s), 3.42 (3H, s) |
| 2.005 | —S(O)CH₃ | (CDCl₃) 7.55-7.63 (1H, m) 7.21-7.29 (2H, m) 6.96-7.02 (1H, m) 3.84 (3H, m) 3.21 (3H, m) |
| 2.006 | —S(O)C₂H₅ | (CDCl₃) 7.54-7.63 (1H, m) 7.16-7.35 (2H, m) 6.92-7.03 (1H, m) 3.85 (3H, m) 3.24-3.43 (2H, m) 1.54 (3H, m) |
| 2.007 | —S(O)₂C₂H₅ | (CDCl₃) 7.62-7.58 (1H, m), 7.27-7.23 (2H, m), 6.96-6.92 (1H, m), 3.95 (3H, s), 3.51 (2H, q), 1.51 (3H, t). |
| 2.008 | —CH₂OCH₃ | (d4MeOH) 7.58-7.54 (1H, m), 7.27-7.22 (2H, m), 7.05-7.01 (1H, m), 4.54 (2H, s), 3.75 (3H, s), 3.47 (3H, s) |

TABLE 2-continued

Examples of herbicidal compounds of the present invention.

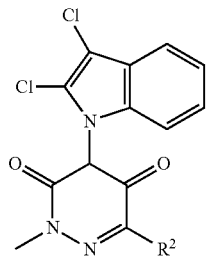

| Compound | R² | NMR |
|---|---|---|
| 2.009 | —CH₂CH(CH₃)₂ | (CDCl₃) 7.55-7.61 (1H, m) 7.23 (2H, dd) 6.88-6.96 (1H, m) 3.73 (3H, s) 2.60 (2H, d) 2.08-2.20 (1H, m) 1.00 (6H, d) |
| 2.010 | -nbutyl | (CDCl₃) 7.56 (1H, d) 7.22 (2H, d) 6.88-6.95 (1H, m) 3.69 (3H, s) 2.64-2.75 (2H, m) 1.68 (2H, dt) 1.36-1.51 (2H, m) 0.98 (3H, t) |
| 2.011 | —CH₂OCH₂-chexyl | (CDCl₃) 7.61-7.57 (1H, m), 7.24-7.20 (2H, m), 7.00-6.96 (1H, m), 4.78 (2H, dd), 3.79 (3H, s), 3.48 (2H, d), 1.75-1.64 (5H, m), 1.30-1.12 (4H, m), 1.01-0.88 (2H, m) |
| 2.012 | —CH₂OCH₂CF₃ | (CDCl₃) 7.58-7.54 (1H, m), 7.24-7.18 (2H, m), 6.85-6.80 (1H, m), 4.62 (2H, dd), 3.93 (2H, q), 3.58 (3H, s) |
| 2.013 | iPr | (CDCl₃) 7.61-7.58 (1H, m), 7.29-7.22 (2H, m), 6.92-6.88 (1H, m), 3.69 (3H, s), 3.18 (1H, septet), 1.30-1.27 (6H, m) |
| 2.014 | —CH₂OiPr | (CDCl₃) 7.58-7.55 (1H, m), 7.23-7.19 (2H, m), 6.97-6.93 (1H, m), 4.76 (2H, s), 3.87 (1H, m), 3.74 (3H, s), 1.28 (6H, d) |
| 2.015 | —CH₂OC₂H₄OCH₃ | (CDCl₃) 7.60-7.56 (1H, m), 7.23-7.19 (2H, m), 6.98-6.94 (1H, m), 4.74 (2H, dd), 3.83-3.81 (2H, m), 3.76 (3H, s), 3.61-3.58 (2H, m), 3.35 (3H, s) |
| 2.016 | —C(=CH₂)CH₃ | (d4MeOH) 7.62-7.53 (1H, m), 7.31-7.23 (2H, m), 7.04 (1H, s), 5.94-5.88 (1H, m), 5.56-5.47 (1H, m), 3.76 (3H, s), 2.23-2.17 (3H, m) |
| 2.017 | —S—C₂H₅ | (d4MeOH) 7.58-7.54 (1H, m), 7.27-7.21 (2H, m), 7.04-7.00 (1H, m), 3.74 (3H, s), 3.12 (2H, q), 1.42 (3H, t) |
| 2.018 | —O-Pr | (DMSO-d6) 7.55-7.51 (1H, m), 7.23-7.19 (2H, m), 7.11-7.07 (1H, m), 4.14 (2H, t), 3.50 (3H, s), 1.78 (2H, m), 1.00 (3H, t) |
| 2.019 | —O—CH₂-iPr | (CDCl₃) 7.60-7.57 (1H, m), 7.24-7.20 (2H, m), 6.98-6.96 (1H, m), 4.10 (2H, d), 3.67 (3H, s), 2.16 (1H, m), 1.05 (6H, d) |
| 2.020 | —O—CH₂CHF₂ | (CDCl₃) 7.58-7.56 (1H, m), 7.23-7.19 (2H, m), 6.95-6.92 (1H, m), 6.11 (1H, tt), 4.47 (2H, td), 3.64 (3H, s) |
| 2.021 | —N(CH₃)₂ | (CDCl₃) 7.61-7.58 (1H, m), 7.25-7.22 (2H, m), 6.98-6.95 (1H, m), 3.71 (3H, s), 2.86 (6H, s) |
| 2.022 | —OCH₃ | (d4MeOH) 7.55-7.51 (1H, m), 7.25-7.19 (2H, m), 7.04-7.00 (1H, m), 4.01 (3H, s), 3.66 (3H, s) |
| 2.023 | —OCH₂CH₃ | (CDCl₃) 7.60-7.57 (1H, m), 7.24-7.20 (2H, m), 6.99-6.96 (1H, m), 4.40 (2H, q), 3.68 (3H, s), 1.48 (3H, t) |
| 2.024 | —OCH₂CF₃ | (d4MeOH) 7.57-7.53 (1H, m), 7.27-7.20 (2H, m), 7.07-7.03 (1H, m), 4.90-4.83 (2H, m), 3.66 (3H, s) |
| 2.025 | —CH₂CH=CH₂ | (d4MeOH) 7.56 (1H, m), 7.26-7.21 (2H, m), 6.99 (1H, m), 6.08 (1H, m), 5.21-5.13 (2H, m), 3.72 (3H, s), 3.51 (2H, dt) |
| 2.026 | -cPr | (CDCl₃) 7.62 (1H, m), 7.29-7.24 (2H, m), 6.96 (1H, m), 3.70 (3H, s), 2.17 (1H, m), 1.08-1.01 (4H, m) |
| 2.027 | —C₂H₅ | (CDCl₃) 7.62 (1H, m), 7.26 (1H, dd), 7.24 (1H, dd), 6.94 (1H, dd), 3.73 (3H, m), 2.75 (2H, q), 1.29 (3H, t) |
| 2.028 | —Br | (CDCl₃) 7.61 (1H, m), 7.28-7.26 (2H, m), 6.94 (1H, m), 3.78 (3H, s) |
| 2.029 | —C(CH₃)OCH₃ | (d6-DMSO) 12.09 (1H, brs), 7.58-7.54 (1H, m), 7.29-7.23 (2H, m), 7.10-7.02 (1H, m), 4.67-4.62 (1H, m), 3.64 (3H, s), 3.30 (3H, d), 1.47-1.44 (3H, m). |
| 2.030 | —CHFCH₃ | (d6-DMSO) 7.58-7.54 (1H, m), 7.28-7.24 (2H, m), 7.10-7.06 (1H, m), 5.88 (1H, dq), 3.66 (3H, s), 1.67 (3H, dd). |
| 2.031 | —CF₂CH₃ | (d6-DMSO) 7.58-7.54 (1H, m), 7.29-7.24 (2H, m), 7.15-7.11(1H, m), 3.66 (3H, s), 2.04 (3H, t). |
| 2.032 | —CH(OH)CH₃ | (d6-DMSO) 7.60-7.56 (1H, m), 7.29-7.24 (2H, m), 7.08-7.02 (1H, m), 5.15-5.09 (1H, m), 3.78 (3H, s), 1.61-1.58 (3H, m). |
| 2.033 | —C(O)CH₃ | (d6-DMSO) 7.58-7.52 (1H, m), 7.27-7.23 (2H, m), 7.19-7.14 (1H, m), 3.80 (3H, s), 2.61 (3H, m). |
| 2.034 | —CH₂CHF₂ | (d4-methanol) 7.61-7.57 (1H, m), 7.29-7.24 (2H, m), 7.06-7.02 (1H, m), 6.35 (1H, tt), 3.76 (3H, s), 3.36 (2H, td). |

TABLE 3

Examples of herbicidal compounds of the present invention.

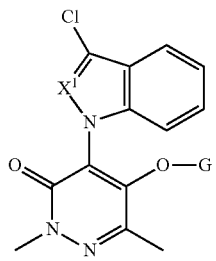

| Compound | X$^1$ | R$^4$ | G | NMR |
|---|---|---|---|---|
| 3.001 | CR$^4$ | —Cl | —C(O)—S-iPr | (CDCl$_3$) 7.52-7.57 (1H, m), 7.21-7.27 (2H, m), 6.94-6.98 (1H, m), 3.86 (3H, s), 3.22 (1H, sept), 2.38 (3H, s), 1.11 (3H, d), 1.04 (3H, d). |
| 3.002 | CR$^4$ | —Cl | —C(O)-morpholinyl | (CDCl$_3$) 7.57-7.61 (1H, m), 7.21-7.25 (2H, m), 6.99-7.03 (1H, m), 3.87 (3H, s), 2.92-3.35 (8H, m), 2.38 (3H, s). |
| 3.003 | CR$^4$ | —Cl | —C(O)-iPr | (CDCl$_3$) 7.55-7.58 (1H, m), 7.21-7.28 (2H, m), 6.96-7.02 (1H, m), 4.61 (1H, sept), 3.85 (3H, s), 2.40 (3H, s), 1.03 (3H, d), 0.98 (3H, d). |
| 3.004 | CR$^4$ | —Cl | —C(O)OCH$_3$ | (CDCl$_3$) 7.55-7.59 (1H, m), 7.22-7.27 (2H, m), 6.95-7.01 (1H, m), 3.86 (3H, s), 3.64 (3H, s), 2.39 (3H, s). |
| 3.005 | N | — | —C(O)OCH$_3$ | (CDCl$_3$) 7.93 (1H, s), 7.71 (1H, d), 7.51 (1H, m), 7.39 (1H, d), 7.32 (1H, t), 3.92 (3H, s), 3.85 (3H, s) |
| 3.006 | N | — | —C(O)CH$_3$ | (CDCl$_3$) 7.85 (1H, s), 7.71 (1H, d), 7.52 (1H, t), 7.38 (1H, d), 7.32 (1H, t), 3.92 (3H, s), 2.19 (3H, s) |
| 3.007 | CR$^4$ | —Cl | —C(O)—S-tButyl | (CDCl$_3$) 7.85 (1H, s), 7.71 (1H, d), 7.52 (1H, t), 7.38 (1H, d), (1H, m), 3.85 (3H, s), 2.38 (3H, s), 1.197.25 (9H, s).), 6.94-6.99 |
| 3.008 | CR$^4$ | —Cl | —C(O)-tButyl | (CDCl$_3$) 7.54-7.58 (1H, m), 7.19-7.25 (2H, m), 6.95-6.99 (1H, m), 3.88 (3H, s), 2.30 (3H, s), 0.91 (9H, s). |
| 3.009 | CR$^4$ | —Cl | —C(O)-p-nitrophenyl | (CDCl$_3$) 8.24 (2H, d), 8.16 (2H, d), 7.48-7.53 (1H, m), 7.13-7.19 (2H, m), 6.95-6.99 (1H, m), 3.68 (3H, s), 2.30 (3H, s). |
| 3.010 | CR$^4$ | —Cl | —C(O)OCH$_2$iPr | (CDCl$_3$) 7.53-7.57 (1H, m), 7.21-7.26 (2H, m), 6.94-6.98 (1H, m), 3.84 (3H, s), 2.34 (3H, s), 1.97-2.30 (2H, m), 1.67-1.77 (1H, m), 0.64 (3H, d), 0.62 (3H, d). |
| 3.011 | CR$^4$ | —Cl | —C(O)OiPr | (CDCl$_3$) 7.55-7.58 (1H, m), 7.21-7.28 (2H, m), 6.96-7.02 (1H, m), 4.61 (1H, sept), 3.85 (3H, s), 2.40 (3H, s), 1.03 (3H, d), 0.98 (3H, d). |

TABLE 4

Examples of herbicidal compounds of the present invention.

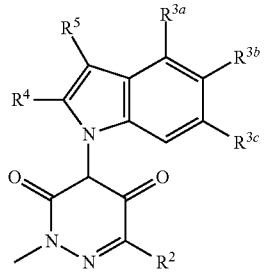

| Compound | R$^2$ | R$^{3a}$ | R$^{3b}$ | R$^{3c}$ | R$^4$ | R$^5$ | NMR |
|---|---|---|---|---|---|---|---|
| 4.001 | H | H | —OCH$_3$ | H | H | H | |
| 4.002 | H | —CF$_3$ | H | H | H | H | |
| 4.003 | H | H | H | —Cl | H | H | |
| 4.004 | H | —Cl | H | H | H | H | |
| 4.005 | H | H | H | F | H | H | |
| 4.006 | H | H | F | H | H | H | |
| 4.007 | H | —F | H | H | H | H | |
| 4.008 | H | H | H | —CH$_3$ | H | H | |
| 4.009 | H | H | —CH$_3$ | H | H | H | |
| 4.010 | H | —CH$_3$ | H | H | H | H | |

TABLE 4-continued

Examples of herbicidal compounds of the present invention.

| Compound | R² | R³ᵃ | R³ᵇ | R³ᶜ | R⁴ | R⁵ | NMR |
|---|---|---|---|---|---|---|---|
| 4.011 | H | H | —OCH₃ | H | Cl | Cl | |
| 4.012 | H | —CF₃ | H | H | Cl | Cl | |
| 4.013 | H | —CF₃ | H | H | H | Cl | |
| 4.014 | H | —Br | H | H | Cl | Cl | |
| 4.015 | H | H | H | Cl | H | Cl | |
| 4.016 | H | H | H | F | Cl | Cl | |
| 4.017 | H | H | F | H | Cl | Cl | |
| 4.018 | H | H | F | H | H | Cl | |
| 4.019 | H | F | H | H | Cl | Cl | |
| 4.020 | H | H | H | —CH₃ | Cl | Cl | |
| 4.021 | H | H | —CH₃ | H | Cl | Cl | |
| 4.022 | H | —CH₃ | H | H | Cl | Cl | |
| 4.023 | H | —CH₃ | H | H | H | Cl | |
| 4.024 | H | H | H | H | Cl | CH₃ | |
| 4.025 | —CH₃ | H | H | H | H | —C≡N | |
| 4.026 | —CH₃ | H | H | H | CH₃ | H | (CDCl₃) 7.53 (1H, m), 7.11 (2H, m), 6.85 (1H, m), 6.55 (1H, bs), 6.42 (1H, s), 3.66 (3H, s), 2.34 (3H, s), 2.19 (3H, d) |
| 4.027 | —CH₃ | H | H | H | CH₃ | Cl | (CDCl₃) 7.56 (1H, d), 7.18 (2H, m), 6.85 (1H, d), 3.61 (3H, s), 2.28 (3H, s), 2.13 (3H, s) |
| 4.028 | —CH₃ | H | H | H | Cl | H | |
| 4.029 | —CH₃ | H | H | H | Br | H | |
| 4.030 | —CHF₂ | H | H | H | Cl | H | |
| 4.031 | —CHF₂ | H | H | H | Br | H | |

Biological Examples

Seeds of a variety of test species are sown in standard soil in pots:—*Solanum nigrum* (SOLNI), *Amaranthus retoflexus* (AMARE), *Setaria faberi* (SETFA), *Alopecurus myosuroides* (ALOMY), *Echinochloa crus-galli* (ECHCG), *Ipomoea hederacea* (IPOHE). After 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/ha. The test plants are then grown in a glasshouse under controlled conditions in a glasshouse (at 24/16° C., day/night; 14 hours light; 65% humidity) and watered twice daily. After 13 days, the test is evaluated for the percentage damage caused to the plant. The biological activities are shown in the following table on a five point scale (5=80-100%; 4=60-79%; 3=40-59%; 2=20-39%; 1=0-19%).

| Compound | POST Application | | | | | |
|---|---|---|---|---|---|---|
| | SOLNI | AMARE | SETFA | ALOMY | ECHCG | IPOHE |
| 1.001 | 5 | 5 | 2 | 1 | 4 | 5 |
| 1.002 | 5 | 4 | 1 | 1 | 1 | 4 |
| 1.003 | 5 | 5 | 1 | 1 | 2 | 5 |
| 1.004 | 4 | 1 | 1 | 1 | 1 | 1 |
| 1.005 | 5 | 2 | 3 | 1 | 1 | 2 |
| 1.006 | 4 | 1 | 1 | 1 | 1 | 1 |
| 1.007 | 5 | 2 | 1 | 1 | 1 | 1 |
| 1.008 | 4 | 1 | 1 | 1 | 1 | 2 |
| 1.009 | 4 | 4 | 1 | 1 | 1 | 1 |
| 1.010 | 3 | 1 | 1 | 1 | 1 | 1 |
| 1.012 | 5 | 5 | 5 | 1 | 2 | 5 |
| 1.013 | 5 | 5 | 2 | 1 | 1 | 5 |
| 1.014 | 5 | 3 | 1 | 1 | 4 | 4 |
| 1.016 | 5 | 2 | 1 | 1 | 1 | 4 |
| 1.017 | 5 | 3 | 1 | 1 | 1 | 4 |
| 1.020 | 5 | 5 | 1 | 1 | 4 | 5 |
| 1.021 | 5 | 5 | 1 | 2 | 2 | 5 |
| 1.022 | 5 | 3 | 1 | 1 | 2 | 5 |
| 1.023 | 5 | 5 | 1 | 2 | 3 | 5 |
| 1.024 | 5 | 5 | 2 | 1 | 2 | 5 |
| 1.025 | 5 | 4 | 1 | 1 | 1 | 3 |
| 1.026 | 5 | 5 | 3 | 2 | 4 | 5 |
| 1.027 | 5 | 4 | 1 | 1 | 3 | 4 |

-continued

| Compound | POST Application | | | | | |
|---|---|---|---|---|---|---|
| | SOLNI | AMARE | SETFA | ALOMY | ECHCG | IPOHE |
| 2.001 | 5 | 3 | 2 | 1 | 2 | 5 |
| 2.002 | 5 | 5 | 1 | 1 | 1 | 5 |
| 2.003 | 2 | 2 | 1 | 1 | 1 | 4 |
| 2.004 | 2 | 2 | 1 | 1 | 1 | 2 |
| 2.005 | 5 | 2 | 1 | 1 | 1 | 5 |
| 2.006 | 4 | 1 | 1 | 1 | 1 | 4 |
| 2.008 | 5 | 3 | 1 | 1 | 1 | 5 |
| 2.009 | 4 | 1 | 1 | 1 | 1 | 2 |
| 2.010 | 4 | 3 | 1 | 1 | 1 | 3 |
| 2.011 | 4 | 2 | 1 | 1 | 1 | 5 |
| 2.012 | 4 | 1 | 1 | 1 | 1 | 4 |
| 2.013 | 4 | 3 | 1 | 1 | 1 | 2 |
| 2.014 | 4 | 2 | 1 | 1 | 1 | 5 |
| 2.015 | 4 | 2 | 1 | 1 | 1 | 5 |
| 2.016 | 4 | 4 | 1 | 1 | 1 | 2 |
| 2.017 | 3 | 4 | 1 | 1 | 2 | 1 |
| 2.018 | 4 | 3 | 1 | 1 | 1 | 4 |
| 2.019 | 4 | 4 | 1 | 1 | 1 | 2 |
| 2.020 | 4 | 4 | 1 | 1 | 1 | 3 |
| 2.021 | 4 | 3 | 1 | 2 | 1 | 3 |
| 2.022 | 5 | 4 | 1 | 1 | 1 | 5 |
| 2.023 | 4 | 2 | 1 | 1 | 1 | 4 |
| 2.024 | 2 | 2 | 1 | 1 | 1 | 1 |
| 2.025 | 5 | 2 | 2 | 1 | 2 | 5 |
| 2.026 | 5 | 4 | 2 | 1 | 1 | 5 |
| 2.027 | 5 | 4 | 1 | 1 | 1 | 5 |
| 2.028 | 5 | 5 | 1 | 1 | 1 | 5 |
| 3.001 | 5 | 5 | 1 | 1 | 1 | 5 |
| 3.002 | 5 | 2 | 1 | 1 | 1 | 5 |
| 3.003 | 5 | 5 | 1 | 1 | 4 | 5 |
| 3.004 | 5 | 5 | 2 | 2 | 4 | 5 |
| 3.005 | 5 | 4 | 1 | 1 | 3 | 5 |
| 3.006 | 5 | 4 | 1 | 2 | 4 | 5 |
| 3.007 | 5 | 5 | 1 | 1 | 1 | 5 |
| 3.008 | 5 | 5 | 1 | 2 | 3 | 5 |
| 3.009 | 5 | 5 | 1 | 1 | 1 | 5 |
| 3.010 | 5 | 5 | 1 | 1 | 3 | 5 |
| 3.011 | 5 | 5 | 2 | 1 | 4 | 5 |
| 4.026 | 5 | 4 | 3 | 2 | 2 | 5 |
| 4.027 | 5 | 5 | 4 | 3 | 5 | 5 |

Comparative Experiment

A comparative experiment is conducted to compare the biological efficacy of a compound of the present invention with those of WO 2011/045271. The test is performed as outlined above using the following compounds. Three different application rates are employed (250 g/ha, 500 g/ha and 1000 g/ha).

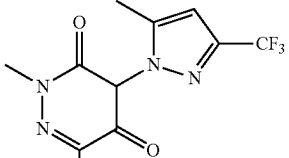

Compound I-a-9 in
WO 2011/045271

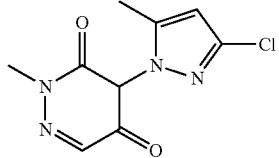

Compound 1.001 of the
present invention

The results observed are summarised in the Table below.

| Compound | Rate g/ha | POST Application | | | | | |
|---|---|---|---|---|---|---|---|
| | | SOLNI | AMARE | SETFA | ALOMY | ECHCG | IPOHE |
| Compound A | 1000 | 5 | 4 | 2 | 2 | 3 | 5 |
| | 500 | 4 | 4 | 1 | 1 | 2 | 5 |
| | 250 | 3 | 3 | 1 | 1 | 1 | 4 |
| Compound B | 1000 | 4 | 4 | 1 | 2 | 2 | 5 |
| | 500 | 3 | 3 | 1 | 1 | 1 | 2 |
| | 250 | 2 | 2 | 1 | 1 | 1 | 1 |
| 1.001 | 1000 | 5 | 4 | 3 | 2 | 3 | 5 |
| | 500 | 5 | 4 | 1 | 2 | 3 | 5 |
| | 250 | 5 | 4 | 1 | 2 | 2 | 5 |

These results show that compounds of the present invention exhibit an increased efficacy vis-à-vis those disclosed in WO2011/045271, which is particularly apparent at lower application rates.

The invention claimed is:

1. A compound of Formula (I):

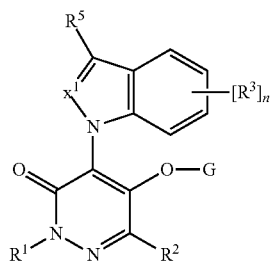

or an agronomically acceptable salt thereof, wherein:—
$X^1$ is N or $CR^4$;
$R^1$ is selected from the group consisting of $C_1$-$C_4$alkyl, $C_1$-$C_2$alkoxy-$C_1$-$C_2$ alkyl, $C_2$-$C_4$alkenyl, $C_1$-$C_4$haloalkyl, $C_2$-$C_4$haloalkenyl, $C_2$-$C_4$alkynyl and $C^2$-$C_4$haloalkynyl;
$R^2$ is selected from the group consisting of hydrogen, halogen, cyano, $C_1$-$C_6$alkyl, $C_1$-$C_6$haloalkyl, $C_1$-$C_6$haloalkoxy, $C_1$-$C_3$haloalkoxy-$C_1$-$C_3$alkyl-, $C_1$-$C_6$alkoxy, $C_1$-$C_3$alkoxy-$C_1$-$C_3$alkyl, $C_1$-$C_3$ alkoxy-$_1$-$C_3$alkoxy-$C_1$-$C_3$alkyl-,$C_3$-$C_6$cycloalkyl, $C_2$-$C_6$ alkenyl, $C_2$-$C_6$ haloalkenyl, $C_2$-$C_6$ alkynyl, $C_1$-$C_6$hydroxyalkyl-, $C_1$-$C_6$alkylcarbonyl-, —S(O)$_p$$C_1$-$C_6$alkyl, amino, $C_1$-$C_6$alkylamino, $C_1$-$C_6$dialkylamino, —C($C_1$-$C_3$alkyl)=N—O—$C_1$-$C_3$alkyl and $C_2$-$C_6$ haloalkynyl;
$R^3$ is independently selected from the group consisting of hydrogen, halogen, nitro, cyano, amino, $C_1$-$C_6$alkyl, $C_1$-$C_6$haloalkyl, $C_3$-$C_6$cycloalkyl, $C_1$-$C_6$alkoxy, $C_1$-$C_6$alkoxycarbonyl and —S(O)$_p$$C_1$-$C_6$ alkyl;
$R^4$ and $R^5$ are independently selected from the group consisting of hydrogen, hydroxyl, halogen, nitro, cyano, amino, $C_1$-$C_6$alkyl, $C_1$-$C_6$haloalkyl, $C_3$-$C_6$cycloalkyl, $C_1$-$C_6$alkoxy, $C_1$-$C_6$alkoxycarbonyl and —S(O)$_p$$C_1$-$C_6$ alkyl;
G is hydrogen or —C(O)—$R^6$;
$R^6$ is selected from the group consisting of $C_1$-$C_6$alkyl, $C_1$-$C_6$alkenyl, $C_1$-$C_6$alkynyl, $C_1$-$C_6$alkyl-S-, $C_1$-$C_6$alkoxy, —N$R^7$ $R^8$ and phenyl optionally substituted by one or more $R^9$;
$R^7$ and $R^8$ are independently selected from the group consisting of $C_1$-$C_6$ alkyl, $C_1$-$C_6$ alkoxy-;
wherein $R^7$ and $R^8$ can together form a morpholinyl ring;
$R^9$ is selected from the group consisting of halogen, cyano, nitro, $C_1$-$C_3$alkyl, $C_1$-$C_3$haloalkyl, $C_1$-$C_3$alkoxy and $C_1$-$C_3$haloalkoxy;
n=0,1,2,3 or 4; and
p=0,1 or 2.

2. The compound according to claim 1, wherein G is hydrogen.

3. The compound of claim 1, wherein $R^2$ is selected from the group consisting of hydrogen, $C_1$-$C_6$alkyl, $C_1$-$C_6$haloalkyl, $C_1$-$C_6$alkoxy, $C_1$-$C_3$alkoxy-$C_1$-$C_3$alkyl, $C_3$-$C_6$cycloalkyl, $C_2$-$C_6$alkenyl, $C_2$-$C_6$haloalkenyl, $C_2$-$C_6$ alkynyl and $C_2$-$C_6$haloalkynyl;

4. The compound according to claim 3, wherein $R^2$ is selected from the group consisting of hydrogen, methyl, ethyl, cyclopropyl and methoxymethyl.

5. The compound according to claim 1, wherein $R^2$ is methyl.

6. The compound according to claim 1, wherein n=0.

7. The compound according to claim 1, wherein $R^1$ is selected from the group consisting of methyl, ethyl and n-propyl.

8. The compound according to claim 1, wherein $X^1$ is N.

9. The compound according to claim 1, wherein $X^1$ is $CR^4$.

10. The compound according to claim 9, wherein $R^4$ is halogen and/or $R^5$ is halogen.

11. A herbicidal composition comprising a herbicidal compound according to claim 1, and an agriculturally acceptable formulation adjuvant.

12. The herbicidal composition according to claim 11, further comprising at least one additional pesticide.

13. The herbicidal composition according to claim 12, wherein the additional pesticide is a herbicide or herbicide safener.

14. A method of controlling weeds at a locus comprising application to the locus of a weed controlling amount of a composition according to claim 11.

15. The compound according to claim 10, wherein $R^5$ is chloro.

16. The compound according to claim 15, wherein $R^4$ is $C_1$-$C_6$haloalkyl or $C_3$-$C_6$cycloalkyl.

17. The compound according to claim 16, wherein $R^4$ is fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl, perfluoro-n-hexyl or cyclopropyl.

* * * * *